(12) United States Patent
Miyazono et al.

(10) Patent No.: US 6,534,476 B2
(45) Date of Patent: Mar. 18, 2003

(54) SMAD6 AND USES THEREOF

(75) Inventors: Kohei Miyazono, Tokyo (JP); Masahiro Kawabata, Tokyo (JP)

(73) Assignee: Japanese Foundation for Cancer Research, Tokyo (JP)

( * ) Notice: Subject to any disclaimer, the term of this patent is extended or adjusted under 35 U.S.C. 154(b) by 0 days.

(21) Appl. No.: 09/923,922

(22) Filed: Aug. 7, 2001

(65) Prior Publication Data

US 2002/0106732 A1 Aug. 8, 2002

Related U.S. Application Data

(62) Division of application No. 09/096,776, filed on Jun. 12, 1998, now Pat. No. 6,270,994
(60) Provisional application No. 60/049,990, filed on Jun. 13, 1997, provisional application No. 60/053,040, filed on Jul. 18, 1997, and provisional application No. 60/066,173, filed on Nov. 18, 1997.

(51) Int. Cl.$^7$ ............................................. C07K 14/00
(52) U.S. Cl. ......................................... 514/2; 530/350
(58) Field of Search ............................... 530/350; 574/2

(56) References Cited

U.S. PATENT DOCUMENTS 5,834,248 A  11/1998  Falb

FOREIGN PATENT DOCUMENTS

| WO | WO96/24604 A | 8/1996 |
| WO | WO97/30065 A | 8/1996 |
| WO | WO97/39105 A | 10/1997 |

OTHER PUBLICATIONS

Roberts et al., *Growth Factors* 8:1–9, 1993.
Lin and Lodish, *Trends Cell Biol.* 11:972–978, 1993.
Derynck, *Trends Biochem. Sci.* 19–:548–553, 1994.
Massague and Weis–Garcia, *Cancer Surv.*, 27:41–64, 1996.
Ten Dijke et al., *Curr. Opin. Cell. Biol.* 8:139–145, 1996.
Wrana et al., *Nature* 370:341–347, 1994.
Weiser et al., *Embo J.* 14:2199–2208, 1995.
Graff et al., *Cell* 85:479–487, 1996.
Sekelsky et al., *Genetics* 139:1347–1358, 1995.
Savage et al., *Proc. Natl. Acad. Sci. USA* 93:790–794, 1996.
Wiersdorff et al., *Development* 122:2153–2163, 1996.
Newfeld et al., *Development* 122:2099–2108, 1996.
Hoodless et al., *Cell* 85:489–500, 1996.
Derynck et al., *Cell* 87:173, 1996.
Wrana and Attisano, *Trends Genet.* 12:493–496, 1996.
Hahn et al., *Science* 271:350–353, 1996.
Riggins et al., *Nature Genet.* 13:347–349, 1996.
Eppert et al., *Cell* 86:543–552, 1996.
Massague, *Cell* 85:947–950, 1996.
Derynck and Zhang, *Curr. Biol.* 6:1226–1229, 1996.
Liu et al., *Nature* 381:620–623, 1996.
Meersseman et al., *Mech. Dev.* 61:127–1400, 1997.
Baker and Harland, *Genes & Dev.* 10:1880–1889, 1996.
Thomsen, *Development* 122:2359–2366, 1996.
Lechleider et al., *J. Biol. Chem.* 271:17617–17620, 1996.
Yingling et al., *Proc. Nat'l Acad. Sci. USA* 93:8940–8944, 1996.
Zhang et al., *Nature* 383:168–172, 1996.
Macias–Silva et al., *Cell* 87:1215–1224, 1996.
Nakao et al., *J. Biol. Chem.* 272:2896–2900, 1996.
Lagna et al., *Nature* 383:832–836, 1996.
Zhang et al., *Curr. Biol.* 7:270–276, 1997.
De Winter et al., *Oncogene* 14:1891–1900, 1997.
Chen et al., *Nature* 383:691–696, 1996.
Imamura et al., *Nature* 389:622–626, 1997.
Massague et al., *Trends Cell Biol.* 7:187–192, 1997.
Yingling et al., *Biochem. Biophys. Acta* 1242:115–136, 1995.
Piccolo et al., *Cell* 86:589–598, 1996.
Zimmerman et al., *Cell* 86:599–606, 1996.
Hemmati–Brivalou et al. *Cell* 77:283–295, 1994.
Yonemori et al., *Am. J. Pathol.* 150:1335–1347, 1997.
Hayashi et al., *Bone* 21:23–30, 1997.
Border and Noble, *N. Engl. J. Med.* 331:1286–1292, 1994.
Feng et al., *J. Biol. Chem.* 270:4237–4245, 1995.

*Primary Examiner*—Karen Cochrane Carlson
(74) *Attorney, Agent, or Firm*—Wolf, Greenfield & Sacks, P.C.

(57) ABSTRACT

The invention includes nucleic acids encoding the Smad6 protein, including fragments and biologically functional variants thereof. Also included are polypeptides and fragments thereof encoded by such nucleic acids, and antibodies relating thereto. Methods and products for using such nucleic acids and polypeptides also are provided.

12 Claims, 16 Drawing Sheets

```
340 G--GEVYAECLSDSSIFVQSRNCNYHHGFHPT-TVCKIPSGCSLKIFNNQEFAQLLAQ--------  Smad1
342 G--GEVFAECLSDSAIFVQSRNCNYHHGFHPT-TVCKIPPGCNLKIFNNQEFAALLAQ--------  Smad2
299 G--GEVFAECLSDSAIFVQSPNCNQRYGWHPA-TVCKIPPGCNLKIFNNQEFAALLAQ--------  Smad3
393 GEGDVWVRCLSDEAVFVQSYYLDREAGRAPGDAVEKIYPSAYIKVFDLRQCHRQMQQAATAQAA-  Smad4
340 G--GEVYAECLSDSSIFVQSRNCNFHHGFHPT-TVCKIPSSCSLKIFNNQEFAQLLAQ--------  Smad5
398 PDG-VWAYNRGEHPIFVNSPTLDAPGGR--ALVVRKVPPGYSIKVFDFERSG--LLQHADAAHGP  Smad6

395 --------------------------------TVYELTKMCTIRMSFVKGWGAEYHRQDVTSTP  Smad1
397 --------------------------------AVYQLTRMCTIRMSFVKGWGAEYRRQTVTSTP  Smad2
354 --------------------------------AVYQLTRMCTIRMSFVKGWGAEYRRQTVTSTP  Smad3
458 AAAQAAAVAGNIPGPGSVGGIAPAISLSAAAAGIGVDDLRRLCILRMSFVKGWGPDYPRQSIKETP  Smad4
395 --------------------------------AVYELTKMCTIRMSFVKGWGAETHRQDVTSTP  Smad5
458 YDPHS---------------------------VRISFAKGWGPCYSRQFITSCP----------R  Smad6

434 CWIEIHLHGPLQWLDKVLTQMGSPHNPISSVS.  Smad1
436 CWIEIHLNGPLQWLDKVLTQMGSPSVRCSSMS.  Smad2
393 CWIELHLNGPLQWLDKVLTQMGSPSIRCSSVS.  Smad3
523 CWIEIHLHRALQLLDEVLHTM--PIADPQPLD.  Smad4
434 CWIEIHLHGPLQWLDKVLTQMGSPLNPISSVS.  Smad5
485 CWLEILNNH-----------------------R  Smad6
```

Fig. 1A - 3

| TβR-I (TD) | - | + | + |
|---|---|---|---|
| M-Smad4 | + | + | + |
| F-Smad3 | + | + | + |
| M-Smad6 | - | - | + |
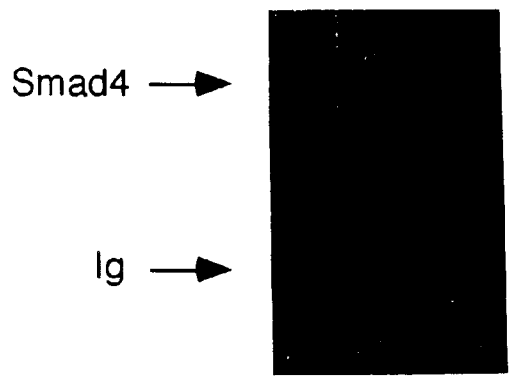
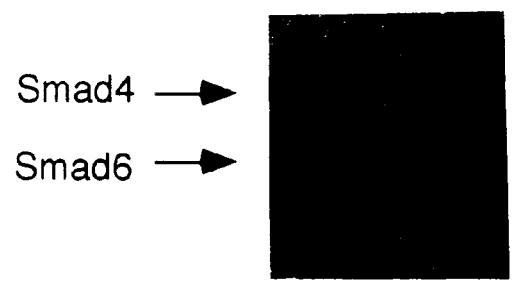
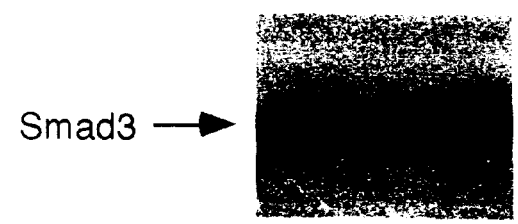
Fig. 4B

| TβR-I (TD) | − | + | + |
|---|---|---|---|
| M-Smad3 | + | + | + |
| F-Smad2 | + | + | + |
| M-Smad6 | − | − | + |
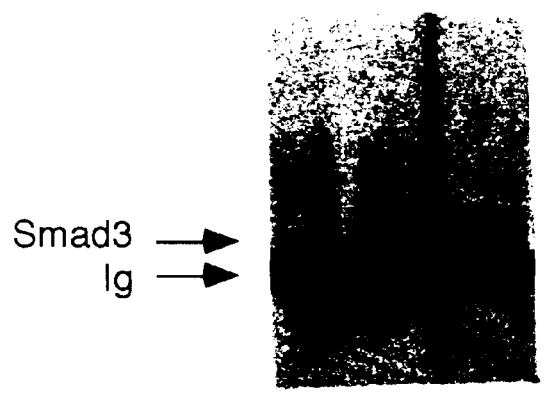
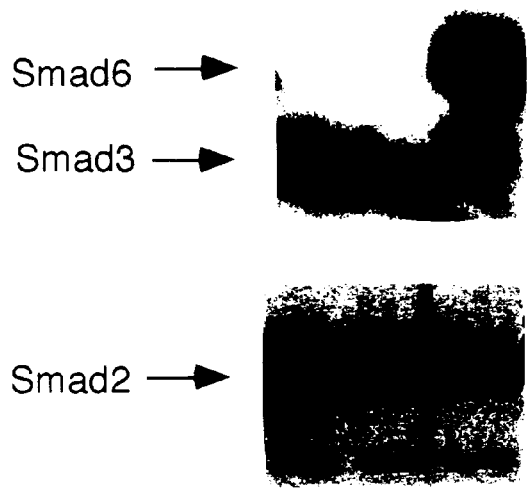
Fig. 4C

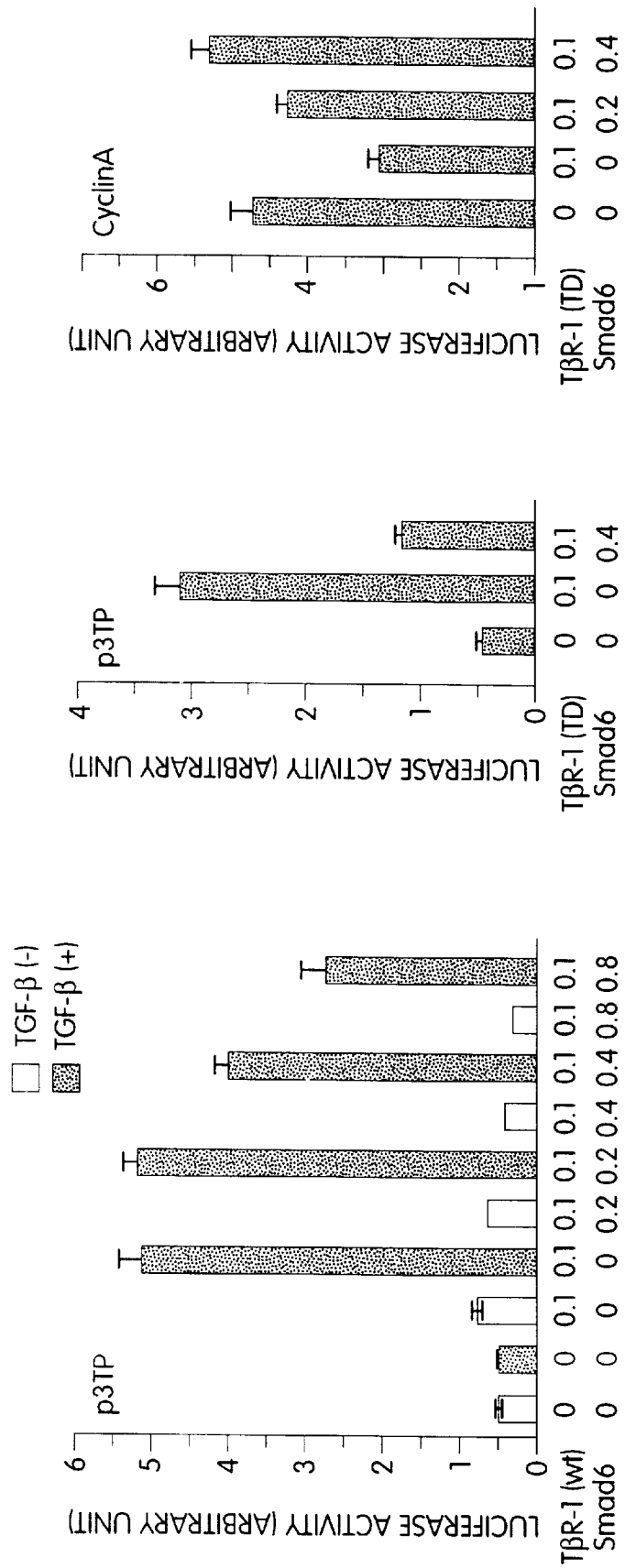

SMAD6 AND USES THEREOF

RELATED APPLICATIONS

This application is a divisional of application Ser. No. 09/096,776, filed Jun. 12, 1998, now U.S. Pat. No. 6,270,994, which claims priority under 35 U.S.C. §119(e) from U.S. provisional application Ser. No. 60/049,990, filed Jun. 13, 1997, from U.S. provisional application Ser. No. 60/053,040, filed Jul. 18, 1997, and from U.S. provisional application Ser. No. 60/066,173, filed Nov. 18, 1997.

FIELD OF THE INVENTION

This invention relates to nucleic acids and encoded polypeptides which interact with the TGF-β superfamily receptor complexes and which are a negative regulators of TGF-β superfamily signalling. The invention also relates to agents which bind the nucleic acids or polypeptides. The invention further relates to methods of using such nucleic acids and polypeptides in the treatment and/or diagnosis of disease.

BACKGROUND OF THE INVENTION

During mammalian embryogenesis and adult tissue homeostasis transforming growth factor β (TGF-β) performs pivotal tasks in intercellular communication (Roberts et al., *Growth Factors* 8:1–9, 1993). The cellular effects of this pleiotropic factor are exerted by ligand-induced hetero-oligomerization of two distantly related type I and type II serine/threonine kinase receptors, TβR-I and TβR-II, respectively (Lin and Lodish, *Trends Cell Biol.* 11:972–978, 1993; Derynck, *Trends Biochem. Sci.* 19-:548–553, 1994; Massague and Weis-Garcia, *Cancer Surv.* 27:41–64, 1996; ten Dijke et al., *Curr. Opin. Cell. Biol.* 8:139–145, 1996). The two receptors, which both are required for signalling, act in sequence; TβR-I is a substrate for the constitutively active TβR-II kinase (Wrana et al., *Nature* 370:341–347, 1994; Weiser et al., *EMBO J.* 14:2199–2208, 1995).

TGF-β is the prototype of a large family of structurally related proteins that are involved in various biological activities (Massague, et al., *Trends Cell Biol.* 7:187–192, 1997; Roberts & Sporn, in: *Peptide growth factors and their receptors, Part I* (Sporn, M. B. and Roberts, A. B., eds) pp. 319–472, Springer-Verlag, Heidelberg (1990); Yingling et al., *Biochim. Biophys. Acta* 1242:115–136, 1995). The TGF-β "superfamily" includes activins and bone morphogenetic proteins (BMPs) that signal in a similar fashion, each employing distinct complexes of type I and type II serine/threonine kinase receptors (Lin and Lodish, 1993; Derynck, 1994; Massague and Weis-Garcia, 1996; ten Dijke et al., 1996). TGF-β related molecules act in environments where multiple signals interact and are likely to be under tight spatial and chronological regulation. For example, activin and BMP exert antagonistic effects in the development of Xenopus embryos (Graff et al., *Cell* 85:479–487, 1996). Chordin (Piccolo et al., *Cell* 86:589–598, 1996) and noggin (Zimmerman et al., *Cell* 86:599–606, 1996), for example, inhibit the ventralizing effect of BMP4 by binding specifically to the ligand. Likewise, follistatin neutralizes the activity of activin (Hemmati-Brivalou et al., *Cell* 77:283–295, 1994).

Genetic studies of TGF-β-like signalling pathways in Drosophila and *Caenorhabditis elegans* have led to the identification of mothers against dpp (Mad) (Sekelsky et al., *Genetics* 139:1347–1358, 1995) and sma (Savage et al., *Proc. Natl. Acad. Sci. USA* 93:790–794, 1996) genes, respectively. The products of these related genes perform essential functions downstream of TGF-β-like ligands acting via serine/threonine kinase receptors in these organisms (Wiersdorff et al., *Development* 122:2153:2163, 1996; Newfeld et al., *Development* 122:2099–2108, 1996; Hoodless et al., *Cell* 85:489–500, 1996). Vertebrate homologs of Mad and sma have been termed Smads (Derynck et al., *Cell* 87:173, 1996) or MADR genes (Wrana and Attisano, *Trends Genet.* 12:493–496, 1996). Genetic alterations in Smad2 and Smad4/DPC4 have been found in specific tumor subsets, and thus Smads may function as tumor suppressor genes (Hahn et al., *Science* 271:350–353, 1996; Riggins et al., *Nature Genet.* 13:347–349,1996; Eppert et al., *Cell* 86:543–552, 1996). Smad proteins share two regions of high similarity, termed MH1 and MH2 domains, connected with a variable proline-rich sequence (Massague, *Cell* 85:947–950, 1996; Derynck and Zhang, *Curr. Biol.* 6:1226–1229, 1996). The C-terminal part of Smad2, when fused to a heterologous DNA-binding domain, was found to have transcriptional activity (Liu et al., *Nature* 381:620–623, 1996; Meersseman et al., *Mech. Dev.* 61:127–1400, 1997). The intact Smad2 protein when fused to a DNA-binding domain, was latent, but transcriptional activity was unmasked after stimulation with ligand (Liu et al., 1996).

Different Smads specify different responses using functional assays in Xenopus. Whereas Smad1 induces ventral mesoderm, a BMP-like response, Smad2 induces dorsal mesoderm, an activin/TGF-β-like response (Graff et al., *Cell* 85:479–487, 1996; Baker and Harland, *Genes & Dev.* 10:1880–1889, 1996; Thomsen, *Development* 122:2359–2366, 1996). Upon ligand stimulation Smads become phosphorylated on serine and threonine residues; BMP stimulates Smad1 phosphorylation, whereas TGF-β induces Smad2 and Smad3 phosphorylation (Hoodless et al., *Cell* 85:489–500, 1996; Liu et al., 1996; Eppert et al., 1996; Lechleider et al., *J. Biol. Chem.* 271:17617–17620, 1996; Yingling et al., *Proc. Nat'l Aced. Sci. USA* 93:8940–8944, 1996; Zhang et al., *Nature* 383:168–172, 1996; Macias-Silva et al., *Cell* 87:1215–1224, 1996; Nakao et al., *J. Biol. Chem.* 272:2896–2900, 1996).

Smad4 is a common component of TGF-β, activin and BMP signalling (Lagna et al., *Nature* 383:832–836, 1996; Zhang et al., *Curr. Biol.* 7:270–276, 1997; de Winter et al., *Oncogene* 14:1891–1900, 1997). Smad4 phosphorylation has thus far been reported only after activin stimulation of transfected cells (Lagna et al., 1996). After stimulation with TGF-β or activin Smad4 interacts with Smad2 or Smad3, and upon BMP challenge a heteromeric complex of Smad4 and Smad1 has been observed (Lagna et al., 1996). Upon ligand stimulation, Smad complexes translocate from the cytoplasm to the nucleus (Hoodless et al., 1996; Liu et al., 1996; Baker and Harland, 1996; Macias-Silva et al., 1996), where they, in combination with DNA-binding proteins, may regulate gene transcription (Chen et al., *Nature* 383:691–696, 1996).

SUMMARY OF THE INVENTION

The invention provides isolated nucleic acid molecules, unique fragments of those molecules, expression vectors containing the foregoing, and host cells transfected with those molecules. The invention also provides isolated polypeptides and agents which bind such polypeptides, including antibodies. The foregoing can be used in the diagnosis or treatment of conditions characterized by the expression of a Smad6 nucleic acid or polypeptide, or lack thereof. The invention also provides methods for identifying pharmacological agents useful in the diagnosis or treatment of such conditions. Here, we present the identification of Smad6, which inhibits phosphorylation of pathway specific Smad polypeptides including Smad2 and Smad1 and inhibits the TGF-β superfamily signalling pathway such as the TGF-β and BMP signalling pathways.

According to one aspect of the invention, an isolated nucleic acid molecule is provided. The molecule hybridizes under stringent conditions to a molecule consisting of the nucleic acid sequence of SEQ ID NO:1. The isolated nucleic acid molecule codes for a polypeptide which inhibits TGF-β, activin, or BMP signalling. The invention further embraces nucleic acid molecules that differ from the foregoing isolated nucleic acid molecules in codon sequence due to the degeneracy of the genetic code. The invention also embraces complements of the foregoing nucleic acids.

In certain embodiments, the isolated nucleic acid molecule comprises a molecule consisting of the nucleic acid sequence of SEQ ID NO:3 or consists essentially of the nucleic acid sequence of SEQ ID NO:1. Preferably, the isolated nucleic acid molecule consists of the nucleic acid sequence of SEQ ID NO:3, According to another aspect of the invention, an isolated nucleic acid molecule is provided. The isolated nucleic acid molecule comprises a molecule consisting of a unique fragment of SEQ ID NO:3 between 12 and 1487 nucleotides in length and complements thereof, provided that the isolated nucleic acid molecule excludes sequences consisting only of SEQ ID NO:4. In one embodiment, the isolated nucleic acid molecule consists of between 12 and 32 contiguous nucleotides of SEQ ID NO:1, or complements of such nucleic acid molecules. In preferred embodiments, the unique fragment is at least 14, 15, 16, 17, 18, 20 or 22 contiguous nucleotides of the nucleic acid sequence of SEQ ID NO:1, SEQ ID NO:3, or complements thereof.

According to another aspect of the invention, the invention involves expression vectors, and host cells transformed or transfected with such expression vectors, comprising the nucleic acid molecules described above.

According to still other aspects of the invention, transgenic non-human animals are provided. The animals include in certain embodiments the foregoing expression vectors. In certain preferred embodiments, the transgenic non-human animal includes a conditional Smad6 expression vector, such as an expression vector that increases expression of Smad6 in a tissue specific, development stage specific, or inducible manner. In other embodiments, the transgenic non-human animal has reduced expression of Smad6 nucleic acid molecules. In some embodiments, the transgenic non-human animal includes a Smad6 gene disrupted by homologous recombination. The disruption can be homozygous or heterozygous. In other embodiments, the transgenic non-human animal includes a conditional Smad6 gene disruption, such as one mediated by e.g. tissue specific, development stage specific, or inducible, expression of a recombinase. In yet other embodiments, the transgenic non-human animal includes a trans-acting negative regulator of Smad6 expression, such as antisense Smad6 nucleic acid molecules, nucleic acid molecules which encode dominant negative Smad6 proteins, Smad6 directed ribozymes, etc.

According to another aspect of the invention, an isolated polypeptide is provided. The isolated polypeptide is encoded by the isolated nucleic acid molecule of any of claims 1, 2, 3, or 4, and the polypeptide has TGF-β, activin, or BMP signalling inhibitory activity. Preferably, the isolated polypeptide consists of the amino acid sequence of SEQ ID NO:2.

In other embodiments, the isolated polypeptide consists of a fragment or variant of the foregoing which retains the activity of the foregoing.

According to another aspect of the invention, there are provided isolated polypeptides which selectively bind a Smad6 protein or fragment thereof, provided that the isolated polypeptide is not a TGF-β superfamily receptor, such as a TGF-β, activin or BMP type I receptor. The isolated polypeptide in certain embodiments binds to a polypeptide encoded by the isolated nucleic acid molecule of any of claims 1, 2, 3, or 4. Preferred isolated polypeptides bind to an epitope defined by a polypeptide consisting of the amino acid sequence of SEQ ID NO:2. In other preferred embodiments, isolated binding polypeptides include antibodies and fragments of antibodies (e.g., Fab, F(ab)$_2$, Fd and antibody fragments which include a CDR3 region which binds selectively to the Smad6 polypeptides of the invention). In still other preferred embodiments, the isolated polypeptide is a monoclonal antibody, a humanized antibody or a chimeric antibody.

The invention provides in another aspect an isolated complex of polypeptides. The isolated complex includes a TGF-β superfamily receptor or receptor complex bound to a polypeptide as claimed in claim 16. Preferably the isolated complex comprises a polypeptide having the amino acid sequence of SEQ ID NO:2. In other preferred embodiments, the receptor or receptor complex is selected from the group consisting of TβRI, BMPR-IA, BMPR-IB, ActR-IA, a complex of TβRI and TβRII, a complex of BMPR-IA and BMPR-II, a complex of BMPR-IB and BMPR-II, a complex of ActR-IA and BMPR-II and a complex of ActR-IA and ActR-II.

According to still another aspect of the invention, methods for reducing TGF-β superfamily signal transduction in a mammalian cell are provided. The methods involve contacting a mammalian cell with an amount of an inhibitor of TGF-β superfamily signal transduction effective to reduce such signal transduction in the mammalian cell. Preferably the TGF-β superfamily signal transduction is mediated by a TGF-β superfamily ligand, particularly TGF-β1, activin, Vg1, BMP-4 and/or BMP-7. Other methods are provided for modulating phosphorylation of pathway specific Smads (e.g. Smad1, Smad2, Smad3 and/or Smad5). Certain methods are provided for reducing phosphorylation of Smad1 or Smad2 in a mammalian cell by contacting the mammalian cell with an agent which reduces Smad1 or Smad2 phosphorylation, respectively. Still other methods are provided for increasing phosphorylation of Smad3 in a mammalian cell by contacting the mammalian cell with an agent which increases Smad3 phosphorylation. In certain embodiments of the foregoing methods, the agent is an isolated Smad6 polypeptide, such as a polypeptide encoded by a nucleic acid which hybridizes under stringent conditions or the nucleic acid of SEQ ID NO:1, or degenerates or complements thereof.

According to still another aspect of the invention, methods for modulating proliferation and/or differentiation of a cancer cell are provided. The methods involve contacting a cancer cell with an amount of an isolated Smad6 polypeptide as described above, effective to reduce proliferation and/or differentiation of the cancer cell.

The invention in a further aspect provides methods for increasing TGF-β superfamily signal transduction in a mammalian cell. The mammalian cell is contacted with an agent that selectively binds to an isolated nucleic acid molecule of the invention or an expression product thereof in an amount effective to increase TGF-β superfamily signal transduction. Preferably the TGF-β superfamily signal transduction is mediated by a TGFβ superfamily ligand selected from the group consisting of TGF-β1, activin, Vg1, BMP-4 and BMP-7. Preferred agents are antisense Smad6 nucleic acids, including modified nucleic acids, and polypeptides including antibodies which bind to a Smad6 polypeptide including the amino acids of SEQ ID NO:2, and a dominant negative variant of the polypeptide of SEQ ID NO:2.

The invention in still another aspect provides compositions comprising a Smad6 polypeptide and a pharmaceutically acceptable carrier.

The invention in a further aspect involves a method for decreasing Smad6 TGF-β superfamily inhibitory activity in a subject. An agent that selectively binds to an isolated nucleic acid molecule of the invention or an expression product thereof is administered to a subject in need of such treatment, in an amount effective to decrease TGFβ superfamily signal transduction inhibitory activity of Smad7 in the subject. Preferably the TGFβ superfamily signal transduction is mediated by a TGFβ superfamily ligand selected from the group consisting of TGF-β, activin, Vg1, BMP-4 and BMP-7. Preferred agents are antisense nucleic acids, including modified nucleic acids, and polypeptides including antibodies which bind to the polypeptide including the amino acids of SEQ ID NO:2, and dominant negative variants of the polypeptide of SEQ ID NO:2.

According to yet another aspect of the invention, methods for treating a condition characterized by abnormal BMP activity are provided. The methods include administering to a subject in need of such treatment an effective amount of Smad6 or a Smad6 agonist or antagonist sufficient to restore the BMP activity to normal. In some embodiments, the condition is selected from the group consisting of ossification of the posterior longitudinal ligament and ossification of the ligament flavum.

According to another aspect of the invention, methods for treating a condition characterized by abnormal TGF-β activity are provided. The methods include administering to a subject in need of such treatment an effective amount of Smad6 or a Smad6 agonist or antagonist sufficient to restore the TGF-β activity to normal. In certain embodiments, the condition is selected from the group consisting of liver fibrosis including cirrhosis and veno-occlusive disease; kidney fibrosis including glomerulonephritis, diabetic nephropathy, allograft rejection and HIV nephropathy; lung fibrosis including idiopathic fibrosis and autoimmune fibrosis; skin fibrosis including systemic sclerosis, keloids, hypertrophic burn scars and eosinophilia-myalgia syndrome; arterial fibrosis including vascular restenosis and atherosclerosis; central nervous system fibrosis including intraocular fibrosis; and other fibrotic diseases including rheumatoid arthritis and nasal polyposis.

In another aspect of the invention, methods for modulating the expression of cyclin A are provided. The methods include contacting a cell with Smad6 or an agonist or antagonist thereof, in an amount effective to modulate the expression of cyclin A. In some embodiments the cell is contacted with Smad6, and the expression of cyclin A is increased. In other embodiments, the cell is contacted with an antagonist of Smad6, and the expression of cyclin A is decreased. Preferably the antagonist of Smad6 is selected from the group consisting of antibodies to Smad6, dominant negative variants of Smad6 and Smad6 antisense nucleic acids.

According to another aspect of the invention, methods are provided for identifying lead compounds for a pharmacological agent useful in the diagnosis or treatment of disease associated with Smad6 TGF-β superfamily signal transduction inhibitory activity. One set of methods involves forming a mixture of a Smad6 polypeptide, a TGF-β superfamily receptor or receptor complex, and a candidate pharmacological agent. The mixture is incubated under conditions which, in the absence of the candidate pharmacological agent, permit a first amount of specific binding of the TGF-β superfamily receptor or receptor complex by the Smad6 polypeptide. A test amount of the specific binding of the TGF-β superfamily receptor or receptor complex by the Smad6 polypeptide then is detected. Detection of an increase in the foregoing activity in the presence of the candidate pharmacological agent indicates that the candidate pharmacological agent is a lead compound for a pharmacological agent which increases the Smad6 TGF-β superfamily signal transduction inhibitory activity. Detection of a decrease in the foregoing activities in the presence of the candidate pharmacological agent indicates that the candidate pharmacological agent is a lead compound for a pharmacological agent which decreases Smad6 TGF-β superfamily signal transduction inhibitory activity. Another set of methods involves forming a mixture as above, adding further a pathway specific Smad polypeptide, and detecting first and test amounts of TGF-β superfamily induced phosphorylation of the pathway specific Smad polypeptide. Detection of an increase in the phosphorylation in the presence of the candidate pharmacological agent indicates that the candidate pharmacological agent is a lead compound for a pharmacological agent which decreases the Smad6 TGF-β superfamily signal transduction inhibitory activity. Detection of a decrease in the foregoing activities in the presence of the candidate pharmacological agent indicates that the candidate pharmacological agent is a lead compound for a pharmacological agent which increases Smad6 TGF-β superfamily signal transduction inhibitory activity. Preferred Smad6 polypeptides include the polypeptides of claim 16. Preferably the TGFβ superfamily receptor is selected from the group consisting of TGFβ superfamily type I receptors, TGFβ superfamily type II receptors, and complexes of TGFβ superfamily type I receptors and TGFβ superfamily type II receptors. Preferred pathway specific Smad polypeptides include Smad1 and Smad2.

According to still another aspect of the invention, methods for increasing phosphorylation of Smad3 in a mammalian cell are provided. The methods include contacting the mammalian cell with an amount of an isolated Smad6 polypeptide effective to increase phosphorylation of Smad3 in the mammalian cell.

According to another aspect of the invention, methods for reducing heteromerization of Smad2 with Smad3 or Smad4 in a mammalian cell are provided. The methods include contacting the mammalian cell with an amount of an isolated Smad6 nucleic acid or polypeptide, or an agonist thereof, effective to reduce heteromerization of Smad2 with Smad3 or Smad4 in the mammalian cell.

The use of the foregoing compositions, nucleic acids and polypeptides in the preparation of medicaments also is provided.

In the foregoing compositions and methods, preferred members of the TGF-β superfamily are TGF-β1, activin, Vg1, BMP-4 and BMP-7, and the preferred pathway specific Smad polypeptides are Smad1, Smad2, Smad3 and Smad5.

These and other objects of the invention will be described in further detail in connection with the detailed description of the invention.

BRIEF DESCRIPTION OF THE FIGURES

Figure 1A-2:
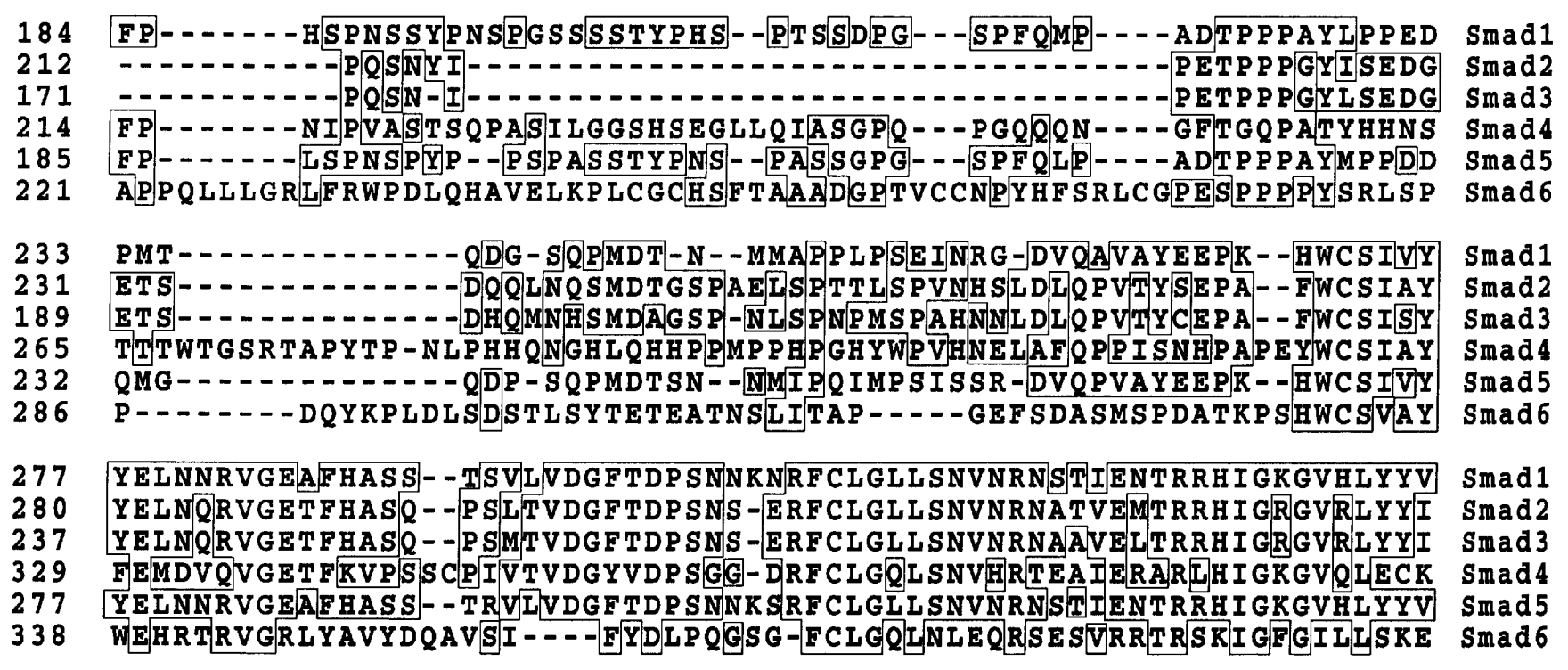

FIGS. 1A-1 to 1A-3 are a representation of a photograph which depicts (A) the protein sequence alignments of Smad6 (SEQ ID NO:2) with Smads 1–5 (SEQ ID NOs:6–10) and FIG. 1B the tissue distribution of mouse and human Smad6 in human (left) and a mouse (right) tissue blots.

FIGS. 4A–4C are a representation of a photograph which demonstrates the effect of Smad6 on the heteromerization of Smad2, Smad3 and Smad4.

FIGS. 5A–5C are a representation of a photograph which shows the effect of Smad6 on transcriptional responses of TGF-β.

BRIEF DESCRIPTION OF THE SEQUENCES

Figure 1B:
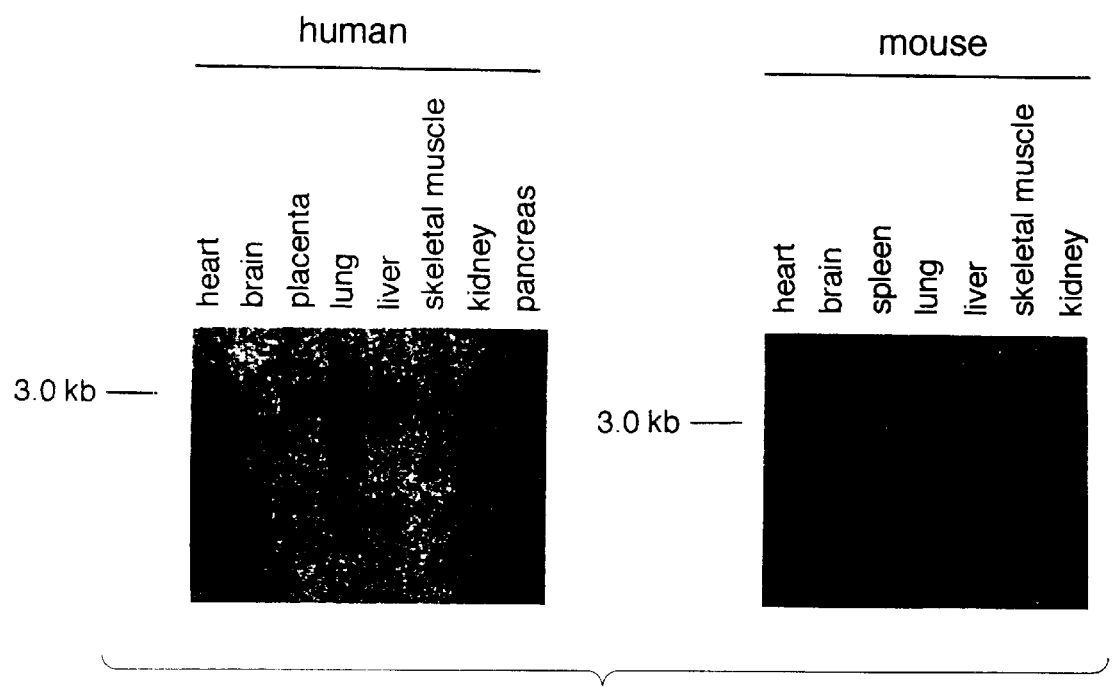

SEQ ID NO:1 is the nucleotide sequence of the mouse Smad6 cDNA.

SEQ ID NO:2 is the amino acid sequence of the mouse Smad6 protein.

SEQ ID NO:3 is the nucleotide sequence of the coding region of the mouse Smad6 cDNA.

SEQ ID NO:4 is the nucleotide sequence of the Smad6-related cDNA having GenBank accession number U59914.

SEQ ID NO:5 is the amino acid sequence of the Smad6-related protein having GenBank accession number U59914.

SEQ ID NO:6 is the amino acid sequence of the Smad1 protein, shown in FIG. 1.

SEQ ID NO:7 is the amino acid sequence of the Smad2 protein, shown in FIG. 1.

SEQ ID NO:8 is the amino acid sequence of the Smad3 protein, shown in FIG. 1.

SEQ ID NO:9 is the amino acid sequence of the Smad4 protein, shown in FIG. 1.

SEQ ID NO:10 is the amino acid sequence of the Smad5 protein, shown in FIG. 1.

DETAILED DESCRIPTION OF THE INVENTION

It has previously been shown that Smad1, Smad2, Smad3, and Smad5 transduce ligand-specific signals. In addition, Smad4 acts as an essential common partner of these ligand-specific Smads. In the present work, Smad6 is reported as a member belonging to a third class of the Smad family. Smad6 has a quite distinct structure from the Smad1, Smad2, Smad3, Smad4 and Smad5, and is believed to be a negative regulator in signaling of the TGF-β superfamily. Although not wishing to be bound by a precise mechanism, it is believed that the regulatory step by Smad6 is at the receptor level since Smad6 stably associates with the type I receptors.

The present invention in one aspect involves the cloning of a cDNA encoding a Smad6 protein which interacts with TGF-β superfamily receptors. The TGF-β superfamily members are well known to those of ordinary skill in the art and include TGF-βs, activins, bone morphogenetic proteins (BMPs), Vg1, Mullerian inhibitory substance (MIS) and growth/differentiation factors (GDFs). The sequence of the mouse Smad6 gene is presented as SEQ ID NO:1, and the predicted amino acid sequence of this gene's protein product is presented as SEQ ID NO:2. Analysis of the sequence by comparison to nucleic acid and protein databases determined that Smad6 has a C-terminal domain (the MH2 domain) which is related to other Smad proteins (FIG. 1).

The invention thus involves in one aspect Smad6 polypeptides, genes encoding those polypeptides, functional modifications and variants of the foregoing, useful fragments of the foregoing, as well as therapeutics relating thereto.

Homologs and alleles of the Smad6 nucleic acids of the invention can be identified by conventional techniques. For example, the human homolog of Smad6 can be isolated by hybridizing a probe derived from SEQ ID NO:1 under stringent conditions a human cDNA library and selecting positive clones. The existence, size, and tissue distribution of a human homolog is demonstrated in the examples by Northern blot. Thus, an aspect of the invention is those nucleic acid sequences which code for Smad6 polypeptides and which hybridize to a nucleic acid molecule consisting of SEQ ID NO:1, under stringent conditions. The term "stringent conditions" as used herein refers to parameters with which the art is familiar. Nucleic acid hybridization parameters maybe found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 65° C.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of Smad6 nucleic acids of the invention. The skilled artisan also is familiar with the methodology for screening cells and libraries for expression of such molecules which then are routinely isolated, followed by isolation of the pertinent nucleic acid molecule and sequencing.

In general, homologs and alleles typically will share at least 40% nucleotide identity and/or at least 50% amino acid identity to SEQ ID NO:1 and SEQ ID NO:2, respectively, in some instances will share at least 50% nucleotide identity and/or at least 65% amino acid identity and in still other instances will share at least 60% nucleotide identity and/or at least 75% amino acid identity. Watson-Crick complements of the foregoing nucleic acids also are embraced by the invention.

In screening for Smad6 proteins, a Southern blot may be performed using the foregoing conditions, together with a radioactive probe. After washing the membrane to which the DNA is finally transferred, the membrane can be placed against X-ray film to detect the radioactive signal.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating Smad6 polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:1 or complements of SEQ ID NO:1. A unique fragment is one that is a 'signature' for the larger nucleic acid. It, for example, is long enough to assure that its precise sequence is not found in molecules outside of the Smad6 nucleic acids defined above. Unique fragments can be used as probes in Southern blot assays to identify such nucleic acids, or can be used in amplification assays such as those employing PCR. As known to those skilled in the art, large probes such as 200 nucleotides or more are preferred for certain uses such as Southern blots, while smaller fragments will be preferred for uses such as PCR. Unique fragments also can be used to produce fusion proteins for generating antibodies or determining binding of the polypeptide fragments, as demonstrated in the Examples, or for generating immunoassay components. Likewise, unique fragments can be employed to produce nonfused fragments of the Smad6 polypeptide, useful, for example, in the preparation of antibodies, in immunoassays, and as a competitive binding partner of the TGF-β receptor, activin receptor or BMP receptor and/or other polypeptides which bind to the Smad6 polypeptides, for example, in therapeutic applications. Unique fragments further can be used as antisense molecules to inhibit the expression of Smad6 nucleic acids and polypeptides, particularly for therapeutic purposes as described in greater detail below.

As will be recognized by those skilled in the art, the size of the unique fragment will depend upon its conservancy in the genetic code. Thus, some regions of SEQ ID NO:1 and its complement will require longer segments to be unique while others will require only short segments, typically between 12 and 32 nucleotides (e.g. 12, 13, 14, 15, 16, 17, 18, 19, 20, 21, 22, 23, 24, 25, 26, 27, 28, 29, 30, 31 and 32 bases long). Excluding nucleic acid molecules consisting completely of the nucleotide sequence of SEQ ID NO:4 or fragments thereof (GenBank accession number U59914) which overlap SEQ ID NO:1, virtually any segment of SEQ ID NO:1, or complements thereof, that is 18 or more nucleotides in length will be unique. A fragment which is completely composed of the sequence of SEQ ID NO:4 or fragments thereof is one which does not include any of the nucleotides unique to Smad6. Preferred longer unique fragments include those which are at least 35, 40, 45, 50, 55, 60, 65, 70, 75, 100, 150, 200, 250, 300, or 500 nucleotide in length. Particularly preferred are those unique fragments drawn completely from the portion of SEQ ID NO:3 which is not overlapped by SEQ ID NO:4.

The unique fragments of the invention exclude sequences identical with certain particular prior art nucleic acids or that are identical to only fragments thereof. It is intended that the claims not embrace such molecules which are in the prior art. For example, portions of prior art ESTs having GenBank accession numbers AA451501, AA046702, W72479, AA131352, AA131266, W41111, N48277, and the like, which are identical to the Smad6 sequence of the invention are not unique fragments of Smad6. Thus, the nucleic acids which consist only of these sequences, or which consist only of fragments of these sequences, are considered to be within the prior art. Nucleic acids, however, which include any portion of the novel sequence of the invention are embraced by the invention, including sequences comprising contiguous portions of the novel sequences and the prior art sequences. Such sequences have unexpected properties, as described herein. In one embodiment the unique fragment does not include any portion of the excluded prior art sequences. Those skilled in the art are well versed in methods for selecting such sequences, typically on the basis of the ability of the unique fragment to selectively distinguish the sequence of interest from non-Smad6 nucleic acids. A comparison of the sequence of the fragment to those on known data bases typically is all that is necessary, although in vitro confirmatory hybridization and sequencing analysis may be performed.

A unique fragment can be a functional fragment. A functional fragment of a nucleic acid molecule of the invention is a fragment which retains some functional property of the larger nucleic acid molecule, such as coding for a functional polypeptide, binding to proteins, regulating transcription of operably linked nucleic acids, and the like. One of ordinary skill in the art can readily determine using the assays described herein and those well known in the art to determine whether a fragment is a functional fragment of a nucleic acid molecule using no more than routine experimentation.

As mentioned above, the invention embraces antisense oligonucleotides that selectively bind to a nucleic acid molecule encoding a Smad6 polypeptide, to increase TGF-β superfamily signalling by reducing the amount of Smad6. This is desirable in virtually any medical condition wherein a reduction of Smad6 is desirable, e.g., to increase TGF-β signalling.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an MRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, although SEQ ID NO:1 discloses a cDNA sequence one of ordinary skill in the art may easily derive the genomic DNA corresponding to the cDNA of SEQ ID NO:1. Thus, the present invention also provides for antisense oligonucleotides which are complementary to the genomic DNA corresponding to SEQ ID NO:1. Similarly, antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding Smad6 polypeptides, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., luciferase, β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Such 5' non-transcribed regulatory sequences especially will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding Smad6 polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Warnier et al., in intradermal injection in mice for immunization against P1A (*Int. J. Cancer,* 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also permits the construction of Smad6 gene transgenics and "knock-outs" in cells and in animals, providing materials for studying certain aspects of TGF-β superfamily signal transduction and the effects thereof on cellular, developmental and physiological processes.

The invention also provides isolated polypeptides, which include the polypeptide of SEQ ID NO:2 and unique fragments of SEQ ID NO:2. Smad6 polypeptides are encoded by nucleic acids described above, e.g., those which hybridize to SEQ ID NO:1. Such polypeptides are useful, for example, alone or as fusion proteins to generate antibodies, as a components of an immunoassay.

A unique fragment of a Smad6 polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of SEQ ID NO:2 will require longer segments to be unique (e.g., 5 20, 30, 50, 75, and 100 amino acid long) while others will require only short segments, typically between 5 and 12 amino acids (e.g. 5, 6, 7, 8, 9, 10, 11 and 12 amino acids long). Virtually any segment of SEQ ID NO:2 which is not overlapped by SEQ ID NO:5, and that is 10 or more amino acids in length will be unique. A unique fragment of a Smad6 polypeptide excludes fragments completely composed of the amino acid sequence of SEQ ID NO:5 which overlaps SEQ ID NO:2. A fragment which is completely composed of the sequence of SEQ ID NO:5 is one which does not include any of the amino acids unique to Smad6.

Unique fragments of a polypeptide preferably are those fragments which retain a distinct functional capability of the polypeptide. Functional capabilities which can be retained in a unique fragment of a polypeptide include interaction with antibodies, interaction with other polypeptides (such as TGF-β superfamily type I receptors) or fragments thereof, selective binding of nucleic acids or proteins, and enzymatic activity. Those skilled in the art are well versed in methods for selecting unique amino acid sequences, typically on the basis of the ability of the unique fragment to selectively distinguish the sequence of interest from non-family members. A comparison of the sequence of the fragment to those on known data bases typically is all that is necessary.

The invention embraces variants of the Smad6 polypeptides described above. As used herein, a "variant" of a Smad6 polypeptide is a polypeptide which contains one or more modifications to the primary amino acid sequence of a Smad6 polypeptide. Modifications which create a Smad6 variant can be made to a Smad6 polypeptide 1) to reduce or eliminate an activity of a Smad6 polypeptide, such as binding to TβR-I; 2) to enhance a property of a Smad6 polypeptide, such as protein stability in an expression system or the stability of protein-protein binding; or 3) to provide a novel activity or property to a Smad6 polypeptide, such as addition of an antigenic epitope or addition of a detectable moiety. Modifications to a Smad6 polypeptide are typically made to the nucleic acid which encodes the Smad6 polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the Smad6 amino acid sequence.

In general, variants include Smad6 polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a Smad6 polypeptide by eliminating proteolysis by proteases in an expression system (e.g., dibasic amino acid residues in yeast expression systems in which KEX2 protease activity is present).

Mutations of a nucleic acid which encode a Smad6 polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant Smad6 polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a Smad6 gene or cDNA clone to enhance expression of the polypeptide. The activity of variants of Smad6 polypeptides can be tested by cloning the gene encoding the variant Smad6 polypeptide into a bacterial or mammalian expression vector, introducing the vector into an appropriate host cell, expressing the variant Smad6 polypeptide, and testing for a functional capability of the Smad6 polypeptides as disclosed herein. For example, the variant Smad6 polypeptide can be tested for inhibition of TβR-I (and/or activin or BMP receptor) signalling activity as disclosed in the Examples, or for inhibition of Smad 1 or Smad2 phosphorylation as is also disclosed herein. Preparation of other variant polypeptides may favor testing of other activities, as will be known to one of ordinary skill in the art.

The skilled artisan will also realize that conservative amino acid substitutions may be made in Smad6 polypeptides to provide functionally equivalent variants of the foregoing polypeptides, i.e, variants which retain the functional capabilities of the Smad6 polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the Smad6 polypeptides include conservative amino acid substitutions of SEQ ID NO:2. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

For example, one can make conservative amino acid substitutions to the amino acid sequence of the Smad6 polypeptide using methods known in the art. Exemplary methods for identifying functional variants of binding peptides are provided in a published PCT application of Strominger and Wucherpfennig (PCT/US96/03182, describes the identification of variants of HLA class II binding peptides). The described methods can be used to identify Smad6 variants which bind TβR-I or other TGF-β superfamily receptors or receptor complexes. These variants can be tested, e.g., for improved stability and are useful, inter alia, in regulation of TGF-β superfamily signalling.

Conservative amino-acid substitutions in the amino acid sequence of Smad6 polypeptides to produce functionally equivalent variants of Smad6 polypeptides typically are made by alteration of the nucleic acid encoding Smad6 polypeptides (SEQ ID NO:1). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a Smad6 polypeptide. Where amino acid substitutions are made to a small unique fragment of a Smad6 polypeptide, such as a TβR-I binding site peptide, the substitutions can be made by directly synthesizing the peptide. The activity of functionally equivalent fragments of Smad6 polypeptides can be tested by cloning the gene encoding the altered Smad6 polypeptide into a bacterial or mammalian expression vector, introducing the vector into an appropriate host cell, expressing the altered Smad6 polypeptide, and testing for a functional capability of the Smad6 polypeptides as disclosed herein. Peptides which are chemically synthesized can be tested directly for function, e.g., for binding to TβR-I.

The invention as described herein has a number of uses, some of which are described elsewhere herein. First, the invention permits isolation of the Smad6 protein molecules (SEQ ID NO:2). A variety of methodologies well-known to the skilled practitioner can be utilized to obtain isolated Smad6 molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating Smad6 polypeptides. These include, but are not limited to, immunochromatography, HPLC, size-exclusion chromatography, ion-exchange chromatography and immune-affinity chromatography.

The invention also makes it possible isolate proteins such as TβR-I, ActR-IB and BMPR-IB by the binding of such proteins to Smad6 as disclosed herein. The identification of this binding also permits one of skill in the art to block the binding of Smad6 to other proteins, such as TβR-I. For example, binding of such proteins can be affected by introducing into a biological system in which the proteins bind (e.g., a cell) a polypeptide including a Smad6 TβR-I binding site in an amount sufficient to reduce or even block the binding of Smad6 and TβR-I. The identification of Smad6 binding to TGF-β superfamily receptors also enables one of skill in the art to isolate Smad6 amino acid sequences which bind to such receptors and prepare modified proteins, using standard recombinant DNA techniques, which can bind to proteins such as TβR-I, ActR-IB and BMPR-IB. For example, when one desires to target a certain protein to a TβR-I receptor complex, one can prepare a fusion polypeptide of the protein and the Smad6 TβR-I binding site. Additional uses are described further herein.

The invention also provides, in certain embodiments, "dominant negative" polypeptides derived from SEQ ID NO:2. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. For example, given the teachings contained herein of a Smad6 polypeptide, one of ordinary skill in the art can modify the sequence of the Smad6 polypeptide by site-specific mutagenesis, scanning mutagenesis, partial gene deletion or truncation, and the like. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected activity (e.g., Smad6 reduction of TGF-β signalling activity) and/or for retention of such an activity. Other similar methods for creating and testing dominant negative variants of a protein will be apparent to one of ordinary skill in the art.

Dominant negative Smad6 proteins include variants in which a portion of the binding site of Smad6 for a TGF-β superfamily receptor has been mutated or deleted to reduce or eliminate Smad6 interaction with the TGF-β receptor complex. Other examples include Smad6 variants in which the ability to inhibit phosphorylation of Smad1, Smad2 and/or Smad3 is reduced. One of ordinary skill in the art can readily prepare Smad6 variants bearing mutations or deletions in the C-terminal domain (e.g., in the MH2 domain) or in the N-terminal domain (e.g., in the glycine/glutamic acid residue rich region) and test such variants for a Smad6 activity.

The invention also involves agents such as polypeptides which bind to Smad6 polypeptides and to complexes of Smad6 polypeptides and binding partners such as TβR-I. Such binding agents can be used, for example, in screening assays to detect the presence or absence of Smad6 polypeptides and complexes of Smad6 polypeptides and their binding partners and in purification protocols to isolate Smad6 polypeptides and complexes of Smad6 polypeptides and their binding partners. Such agents also can be used to inhibit the native activity of the Smad6 polypeptides or their binding partners, for example, by binding to such polypeptides, or their binding partners or both.

The invention, therefore, embraces peptide binding agents which, for example, can be antibodies or fragments of antibodies having the ability to selectively bind to Smad6 polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modem Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to Smad6 polypeptides, and complexes of both Smad6 polypeptides and their binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties (e.g., peptidomimetics).

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the Smad6 polypeptide. This process can be repeated through several cycles of reselection of phage that bind to the Smad6 polypeptide. Repeated rounds lead to enrichment of phage bearing particular sequences. DNA sequence analysis can be conducted to identify the sequences of the expressed polypeptides. The minimal linear portion of the sequence that binds to the Smad6 polypeptide can be determined. One can repeat the procedure using a biased library containing inserts containing part or all of the minimal linear portion plus one or more additional degenerate residues upstream or downstream thereof Yeast two-hybrid screening methods also may be used to identify polypeptides that bind to the Smad6 polypeptides. Thus, the Smad6 polypeptides of the invention, or a fragment thereof, can be used to screen peptide libraries, including phage display libraries, to identify and select peptide binding partners of the Smad6 polypeptides of the invention. Such molecules can be used, as described, for screening assays, for purification protocols, for interfering directly with the functioning of Smad6 and for other purposes that will be apparent to those of ordinary skill in the art.

A Smad6 polypeptide, or a fragment thereof, also can be used to isolate their native binding partners, including, e.g., the TGF-$\beta$ receptor complex. Isolation of such binding partners may be performed according to well-known methods. For example, isolated Smad6 polypeptides can be attached to a substrate (e.g., chromatographic media, such as polystyrene beads, or a filter), and then a solution suspected of containing the TGF-$\beta$ receptor complex may be applied to the substrate. If a TGF$\beta$ receptor complex which can interact with Smad6 polypeptides is present in the solution, then it will bind to the substrate-bound Smad6 polypeptide. The TGF-$\beta$ receptor complex then may be isolated. Other proteins which are binding partners for Smad6, such as other Smads, and activin or BMP receptor complexes, may be isolated by similar methods without undue experimentation.

It will also be recognized that the invention embraces the use of the Smad6 cDNA sequences in expression vectors, as well as to transfect host cells and cell lines, be these prokaryotic (e.g., E. coli), or eukaryotic (e.g., CHO cells, COS cells, yeast expression systems and recombinant baculovirus expression in insect cells). Especially useful are mammalian cells such as human, mouse, hamster, pig, goat, primate, etc. They may be of a wide variety of tissue types, and include primary cells and cell lines. Specific examples include keratinocytes, fibroblasts, COS cells, peripheral blood leukocytes, bone marrow stem cells and embryonic stem cells. The expression vectors require that the pertinent sequence, i.e., those nucleic acids described supra, be operably linked to a promoter.

The isolation of the Smad6 gene also makes it possible for the artisan to diagnose a disorder characterized by aberrant expression of Smad6. These methods involve determining expression of the Smad6 gene, and/or Smad6 polypeptides derived therefrom. In the former situation, such determinations can be carried out via any standard nucleic acid determination assay, including the polymerase chain reaction, or assaying with labeled hybridization probes.

The invention further provides methods for reducing or increasing TGF-$\beta$ superfamily signal transduction in a cell. Such methods are useful in vitro for altering the TGF-$\beta$ signal transduction, for example, in testing compounds for potential to block aberrant TGF-$\beta$ signal transduction or increase deficient TGF-$\beta$ signal transduction. In vivo, such methods are useful for modulating growth, e.g., to treat cancer and fibrosis. Increasing TGF-$\beta$ signal transduction in a cell by, e.g., introducing a dominant negative Smad6 polypeptide or Smad6 antisense oligonucleotides in the cell, can be used to provide a model system for testing the effects of putative inhibitors of TGF-$\beta$ signal transduction. Such methods also are useful in the treatment of conditions which result from excessive or deficient TGF-$\beta$ signal transduction. TGF-$\beta$ signal transduction can be measured by a variety of ways known to one of ordinary skill in the art, such as the reporter systems described in the Examples. Various modulators of Smad6 activity can be screened for effects on TGF-$\beta$ signal transduction using the methods disclosed herein. The skilled artisan can first determine the modulation of a Smad6 activity, such as TGF-$\beta$ signalling activity, and then apply such a modulator to a target cell or subject and assess the effect on the target cell or subject. For example, in screening for modulators of Smad6 useful in the treatment of cancer, cells in culture can be contacted with Smad6 modulators and the increase or decrease of growth or focus formation of the cells can be determined according to standard procedures. Smad6 activity modulators can be assessed for their effects on other TGF-$\beta$ signal transduction downstream effects by similar methods in many cell types.

Thus it can be of therapeutic benefit to administer Smad6 protein or nucleic acid encoding a Smad6 protein, or an agonist or antagonist of Smad6, to modulate TGF-$\beta$ superfamily activity in certain conditions characterized by abnormal TGF-$\beta$ superfamily activity. Specific examples of conditions involving abnormally elevated BMP activity include ossification of the posterior longitudinal ligament (Yonemori et al., Am. J. Pathol. 150:1335–1347, 1997) and ossification of the ligament flavum (Hayashi et al., Bone 21:23–30, 1997). Specific examples of conditions involving abnormal TGF-$\beta$ activity include liver fibrosis including cirrhosis and veno-occlusive disease; kidney fibrosis including glomerulonephritis, diabetic nephropathy, allograft rejection and HIV nephropathy; lung fibrosis including idiopathic fibrosis and autoimmune fibrosis; skin fibrosis including systemic sclerosis, keloids, hypertrophic bum scars and eosinophilia-myalgia syndrome; arterial fibrosis including vascular restenosis and atherosclerosis; central nervous system fibrosis including intraocular fibrosis; and other fibrotic diseases including rheumatoid arthritis and nasal polyposis. (see, e.g., Border and Noble, N. Engl. J. Med. 331:1286–1292, 1994).

An effective amount of Smad6, or an antagonist thereof, is administered to treat the condition, which amount can be determined by one of ordinary skill in the art by routine experimentation. For example, to determine an effective amount of Smad6 for treating ossification, Smad6 can be administered and the progress of the ossification monitored using standard medical diagnostic methods. An amount of Smad6 which reduces the progression of the ossification, or even halts the progression of the ossification is an effective amount. The person of ordinary skill in the art will be familiar with such methods. Other conditions involving abnormally elevated or reduced TGF-β superfamily activity can be treated in a like manner, by administering Smad6 or an agonist thereof, or a Smad6 antagonist, respectively, to reduce or elevate the TGF-β superfamily activity into normal ranges as needed. Smad6 antagonists include the antibodies to Smad6, dominant negative variants of Smad6 and antisense Smad6 nucleic acids described above. Smad6 agonists include agents which increase Smad6 expression, binding or activity.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences,* 18th edition, 1990, pp 1694–1712; incorporated by reference). Those of skill in the art can readily determine the various parameters and conditions for producing antibody aerosols without resort to undue experimentation. When using antisense preparations of the invention, slow intravenous administration is preferred.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The preparations of the invention are administered in effective amounts. An effective amount is that amount of a pharmaceutical preparation that alone, or together with further doses, produces the desired response. For example, in the case of treating cancer, the desired response is inhibiting the progression of the cancer. In the case of treating ossification of the ligamentum flavum, the desired response is inhibiting the progression of the ossification. This may involve only slowing the progression of the disease temporarily, although more preferably, it involves halting the progression of the disease permanently. This can be monitored by routine methods or can be monitored according to diagnostic methods of the invention discussed herein.

The invention also contemplates gene therapy. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

The invention further provides efficient methods of identifying pharmacological agents or lead compounds for agents active at the level of a Smad6 or Smad6 fragment modulatable cellular function. In particular, such functions include TGF-β, activin and BMP signal transduction and formation of a TGF-β superfamily receptor-Smad6 protein complex. Generally, the screening methods involve assaying for compounds which interfere with a Smad6 activity such as TGF-β receptor-Smad6 binding, etc. Such methods are adaptable to automated, high throughput screening of compounds. The target therapeutic indications for pharmacological agents detected by the screening methods are limited only in that the target cellular function be subject to modulation by alteration of the formation of a complex comprising a Smad6 polypeptide or fragment thereof and one or more natural Smad6 intracellular binding targets, such as TGF-β receptor. Target indications include cellular processes modulated by TGF-β, activin and BMP signal transduction following receptor-ligand binding.

A wide variety of assays for pharmacological agents are provided, including, labeled in vitro protein-protein binding assays, electrophoretic mobility shift assays, immunoassays, cell-based assays such as two- or three-hybrid screens, expression assays, etc. For example, three-hybrid screens are used to rapidly examine the effect of transfected nucleic acids on the intracellular binding of Smad6 or Smad6 fragments to specific intracellular targets. The transfected nucleic acids can encode, for example, combinatorial peptide libraries or antisense molecules. Convenient reagents for such assays, e.g., GAL4 fusion proteins, are known in the art. An exemplary cell-based assay involves transfecting a cell with a nucleic acid encoding a Smad6 polypeptide fused to a GAL4 DNA binding domain and a nucleic acid encoding a TGF-β receptor domain which interacts with Smad6 fused to a transcription activation domain such as VP16. The cell also contains a reporter gene operably linked to a gene expression regulatory region, such as one or more GAL4 binding sites. Activation of reporter gene transcription occurs when the Smad6 and TGF-β receptor fusion polypeptides bind such that the GAL4 DNA binding domain and the VP16 transcriptional activation domain are brought into proximity to enable transcription of the reporter gene.

Agents which modulate a Smad6 polypeptide mediated cell function are then detected through a change in the expression of reporter gene. Methods for determining changes in the expression of a reporter gene are known in the art.

Smad6 fragments used in the methods, when not produced by a transfected nucleic acid are added to an assay mixture as an isolated polypeptide. Smad6 polypeptides preferably are produced recombinantly, although such polypeptides may be isolated from biological extracts. Recombinantly produced Smad6 polypeptides include chimeric proteins comprising a fusion of a Smad6 protein with another polypeptide, e.g., a polypeptide capable of providing or enhancing protein-protein binding, sequence specific nucleic acid binding (such as GAL4), enhancing stability of the Smad6 polypeptide under assay conditions, or providing a detectable moiety, such as green fluorescent protein or Flag epitope as provided in the examples below.

The assay mixture is comprised of a natural intracellular Smad6 binding target such as a TGF-β receptor or fragment thereof capable of interacting with Smad6. While natural Smad6 binding targets may be used, it is frequently preferred to use portions (e.g., peptides or nucleic acid fragments) or analogs (i.e., agents which mimic the Smad6 binding properties of the natural binding target for purposes of the assay) of the Smad6 binding target so long as the portion or analog provides binding affinity and avidity to the Smad6 fragment measurable in the assay.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, antimicrobial agents, and the like may also be used.

The mixture of the foregoing assay materials is incubated under conditions whereby, but for the presence of the candidate pharmacological agent, the Smad6 polypeptide specifically binds the cellular binding target, a portion thereof or analog thereof. The order of addition of components, incubation temperature, time of incubation, and other perimeters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the Smad6 polypeptide and one or more binding targets is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromatographic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of Smad6 polypeptide interacting with a target molecule typically encodes a directly or indirectly detectable product, e.g., β-galactosidase activity, luciferase activity, and the like. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseradish peroxidase, etc.). The label may be bound to a Smad6 binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The invention provides Smad6-specific binding agents, methods of identifying and making such agents, and their use in diagnosis, therapy and pharmaceutical development. For example, Smad6-specific pharmacological agents are useful in a variety of diagnostic and therapeutic applications, especially where disease or disease prognosis is associated with improper utilization of a pathway involving Smad6, e.g., TGF-β induced phosphorylation of Smad1 or Smad2, TGF-β superfamily receptor-Smad6 complex formation, etc. Novel Smad6-specific binding agents include Smad6-specific antibodies and other natural intracellular binding agents identified with assays such as two hybrid screens, and non-natural intracellular binding agents identified in screens of chemical libraries and the like.

In general, the specificity of Smad6 binding to a binding agent is shown by binding equilibrium constants. Targets which are capable of selectively binding a Smad6 polypeptide preferably have binding equilibrium constants of at least about $10^7 M^{-1}$, more preferably at least about $10^8 M^{-1}$, and most preferably at least about $10^9 M^{-1}$. The wide variety of cell based and cell free assays may be used to demonstrate Smad6-specific binding. Cell based assays include one, two and three hybrid screens, assays in which Smad6-mediated transcription is inhibited or increased, etc. Cell free assays include Smad6-protein binding assays, immunoassays, etc. Other assays useful for screening agents which bind Smad6 polypeptides include fluorescence resonance energy transfer (FRET), and electrophoretic mobility shift analysis (EMSA).

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

EXAMPLES

Methods

Cloning of Mouse Smad6 and Northern Blot

A mouse lung cDNA library (Stratagene, La Jolla, Calif.) was screened with an EST clone (clone ID 429356) as a probe. One of the clones contained the entire coding region of the mouse Smad6 and was sequenced using an ALFred sequencer (Pharmacia Biotech) and a Sequenase sequencing kit (USB, Cleveland, Ohio). Sequence analysis was done with DNASTAR (DNASTAR, Inc.). Human and mouse tissue blots (Clontech, Palo Alto, Calif.) were probed with the EST clone.

Plasmids

Mammalian expression vectors with an amino-terminal tag (FLAG or Myc) were constructed by inserting oligonucleotides encoding the epitope-tag sequence into pcDNA3 (Invitrogen). The coding region of the mouse Smad6 was amplified by PCR and subcloned into Myc-pcDNA3 or FLAG-pcDNA3. The integrity of the products were confirmed by sequencing. Smad1, Smad2, Smad3 and Smad4 expression plasmids were constructed in a similar manner.

Affinity Cross-linking and Immunoprecipitation

Iodination of TGF-β1 (R&D Systems), activin A (gift of Y. Eto), and OP1/BMP-7 (gift of T. K. Sampath) and the following immunoprecipitation were performed as described (Okadome et al., *J. Biol. Chem.* 271:21687–21690, 1996).

Western Blot and in vivo Phosphorylation

COS-7 cells were transiently transfected using DMRIE-C (Gibco/BRL, Gaithersburg, Md.). [$^{32}$P]orthophosphate- or [$^{35}$S]methionine/cysteine-labeling and immunoprecipitation were done as described by Nakao et al. (*J. Biol. Chem.* 272:2896–2900, 1997). For Western blot of the immunoprecipitated proteins, tagged proteins were detected by chemiluminescence (ECL, Amersham, Arlington Heights, Ill.).

Luciferase Assays

Mink R mutant cells were transiently transfected with an appropriate combination of a reporter, expression plasmids, and pcDNA3 using Tfx-50 (Promega). Total amounts of transfected DNA were the same in each experiment, and values were normalized using sea pansy luciferase activity under the control of the thymidine kinase promoter (pRL-TK, Toyo Ink).

Cell Cultures

C1C12 cells, F9 cells, and ST2 cells were obtained from Riken Cell Bank (Tsukuba, Japan). 10T1/2 cells were from American Type Culture Collection (Bethesda, Md., USA). C1C12 cells and 10T1/2 cells were cultured in Dulbecco's modified Eagle's medium (DMEM) with 10% FBS, 100 units of penicillin and 50 μg of streptomycin per ml. F9 cells were cultured in DMEM with 15% FBS and the antibiotics, and ST2 cells were cultured in RPMI1640 with 10% FBS and the antibiotics. The cells were kept in 5% $CO_2$ humid atmosphere at 37° C.

Poly(A)$^+$ RNA Isolation and Northern Blotting

Poly(A$^+$) RNA was obtained using Oligotex dT-30 Super latex beads (Takara Shuzo Co., Ltd.) according to the manufacturer's method. Poly(A)$^+$ RNA (3 μg) from cells treated with BMP-2 (300 ng/ml), BMP-7/OP-1(300 ng/ml), or TGF-β (25 ng/ml) for various time periods were electrophoresed in 1% gel in the presence of 2.2 M formaldehyde gels and blotted to Hybond N membranes (Amersham). The complete coding region of mouse Smad6 cDNA was labeled by [α-$^{32}$P]dCTP using Random Primer Labeling Kit (Takara Shuzo Co., Ltd.). Hybridization was performed in a solution containing 5×SSC, 1% SDS, 5×Denhardt's solution and 10 μg/ml salmon sperm DNA at 65° C. with 2×SSC, 1% SDS for 20 min. twice, 0.5×SSC, 1% SDS for 30 min. 0.2×SSC, 1% SDS for 10 min. The filters were stripped by boiled distilled water containing 0.1% SDS and rehybridized.

Example 1

Identification of Smad6 and Determination of its Expression

In search of new members of the Smad family, several expressed-sequence tag (EST) sequences that are not ascribed to the five mammalian Smads characterized previously (Massagué et al., 1997) were identified. We screened a mouse lung cDNA library using one of the EST clones (clone ID 429356) as a probe and identified overlapping clones encoding the same protein of 495 amino acids with a predicted molecular weight of 53.7 kDa (FIG. 1a, SEQ ID NO:2; GenBank accession number AF010133). Identical residues are boxed. The C-terminal amino acid sequence of the protein was almost identical with the entire protein sequence of a GenBank clone deposited as the human Smad6 (235 amino acids, accession number: U59914). It thus was concluded that our clone is the full-length mouse Smad6. Chromosomal localization of the human Smad6 (JV15-1) has been reported (Riggins et al., Nature Genet. 13:347–349, 1996). Except for the human Smad6, all of the Smads, including Drosophila and C. elegans Smads, comprise conserved N-terminal and C-terminal regions (MH1 and MH2, respectively) separated by a proline-rich linker region of variable length and sequence, although Smad4 has a unique insert in its MH2 region (Massagué, et al., 1997). The C-terminal one-third of Smad6 shares the conserved sequence with the MH2 regions of the other Smads, whereas its N-terminal region shows a striking difference from the conserved MH1 sequence (FIG. 1a), suggesting a novel function of this molecule.

Northern blot analysis of various human and mouse tissues, using the human EST clone 429356 as a probe, revealed relatively ubiquitous expression of the mRNA species of 3.0 kb with the highest expression in lung (FIG. 1b; human (left) and mouse (right)).

Example 2

Receptor Binding of Smad6

Members of the TGF-β superfamily exert their diverse effects through binding to two types of receptors with serine-threonine kinase activity (Yingling et al., Biochim. Biophys. Acta 1242:115–136, 1995). The ligand first binds to the type II receptor, which consequently activates the type I receptor by direct phosphorylation. The activated type I receptor then phosphorylates ligand-specific Smads such as Smad1, Smad2, and Smad3 (Massagué, et al., 1997; Zhang et al., Nature 383:168–172, 1996; Lagna et al., Nature 383:832–836, 1996; Macias-Silva et al., Cell 87:1215–1224, 1996). The association of Smad2 with TβR-I requires activation of TβR-I requires activation of TβR-1 by the type II receptor (TβR-II) (Macias-Silva et al., 1996). Smad2, however, interacts with TβR-I only transiently under physiological conditions, since Smad2 is released from TβR-I after phosphorylation by the receptor. The interaction of Smad2 with the TβR-I has thus been observed only when the kinase-defective form of TβR-I is used (Macias-Silva et al., 1996). It should be noted that Smad4 does not associate the receptors (Zhang et al., 1996).

Figure 2A:
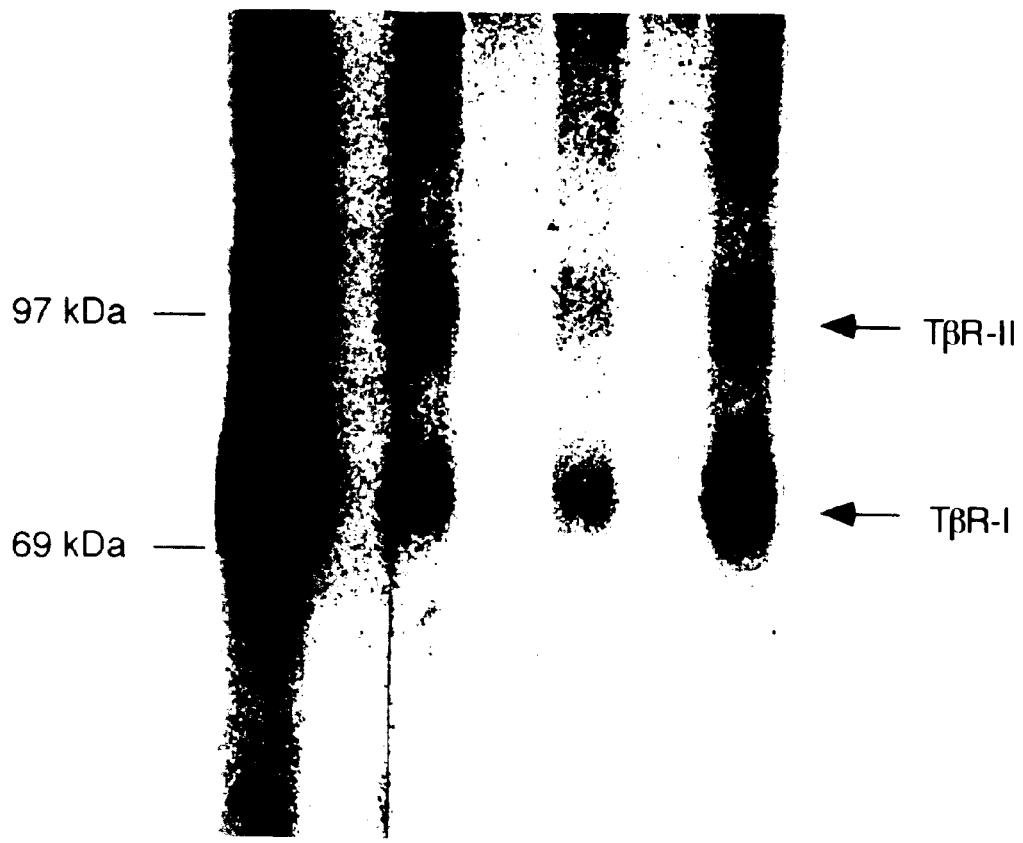
FIGS. 2A–2C are a representation of a photograph which shows the binding of Smad6 to type I receptors; (A) TβR-I, (B) ActR-IB, (C) BMPR-IB.

The interaction of Smad6 with the type I receptors was examined in affinity cross-linking assays. COS-7 cells were transfected with FLAG-tagged Smad6 (F-Smad6) or FLAG-tagged Smad2 (F-Smad2) in combination with the wild type (wt) or kinase-defective (KR) HA-tagged TβR-I and hexahistidine-tagged TβR-II. Cells were affinity labeled with $^{125}$I-TGF-β1 and lysates were immunoprecipitated with anti-HA antibody or anti-FLAG M2 antibody. Immune complexes were subjected to SDS-PAGE and autoradiography. Smad6 bound to both wild type and kinase-defective TβR-I depending on the kinase activity of TβR-II. In contrast, Smad2 bound to kinase-defective TβR-I but not to the wild type TPR-1. Smad6 bound to the TGF-β receptor complexes as revealed by the coprecipitation of the receptor complexes with Smad6 (FIG. 2a). Similarly to Smad2, the binding of Smad6 to TβR-I required the kinase activity of TβR-II (FIG. 2a). Smad6, however, stably bound to the wild type TβR-I.

Figure 2B:
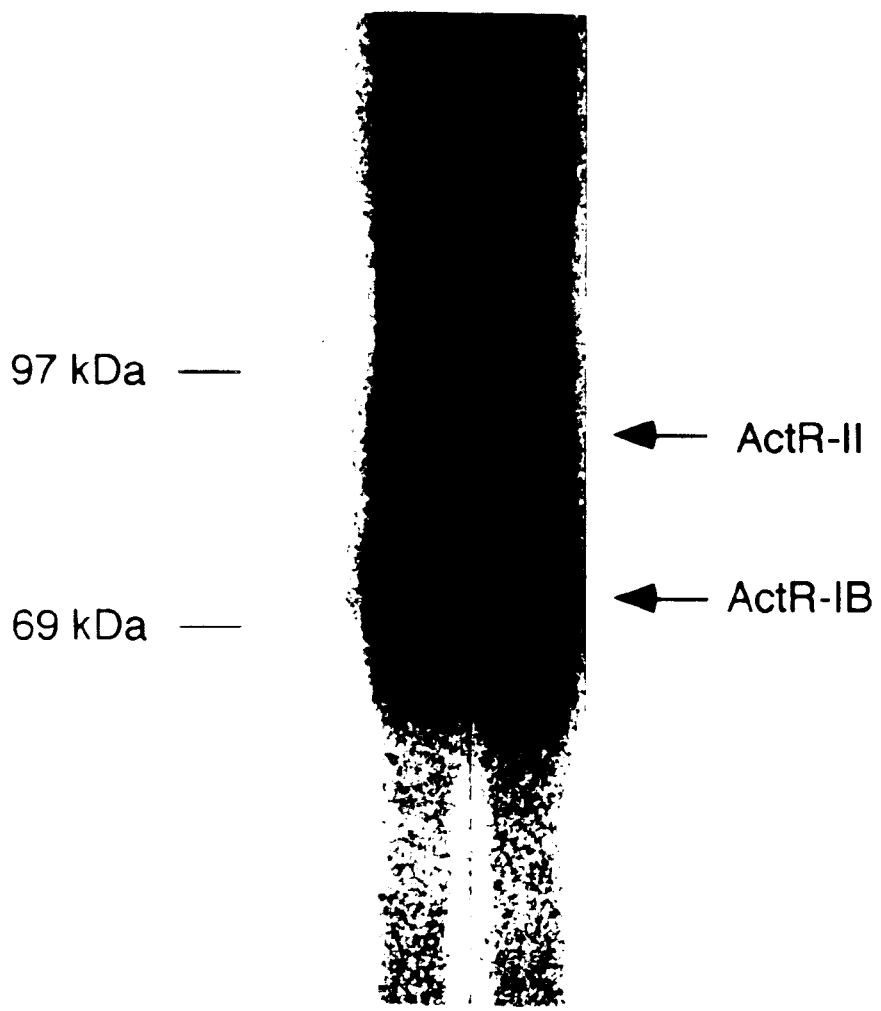
Figure 2C:
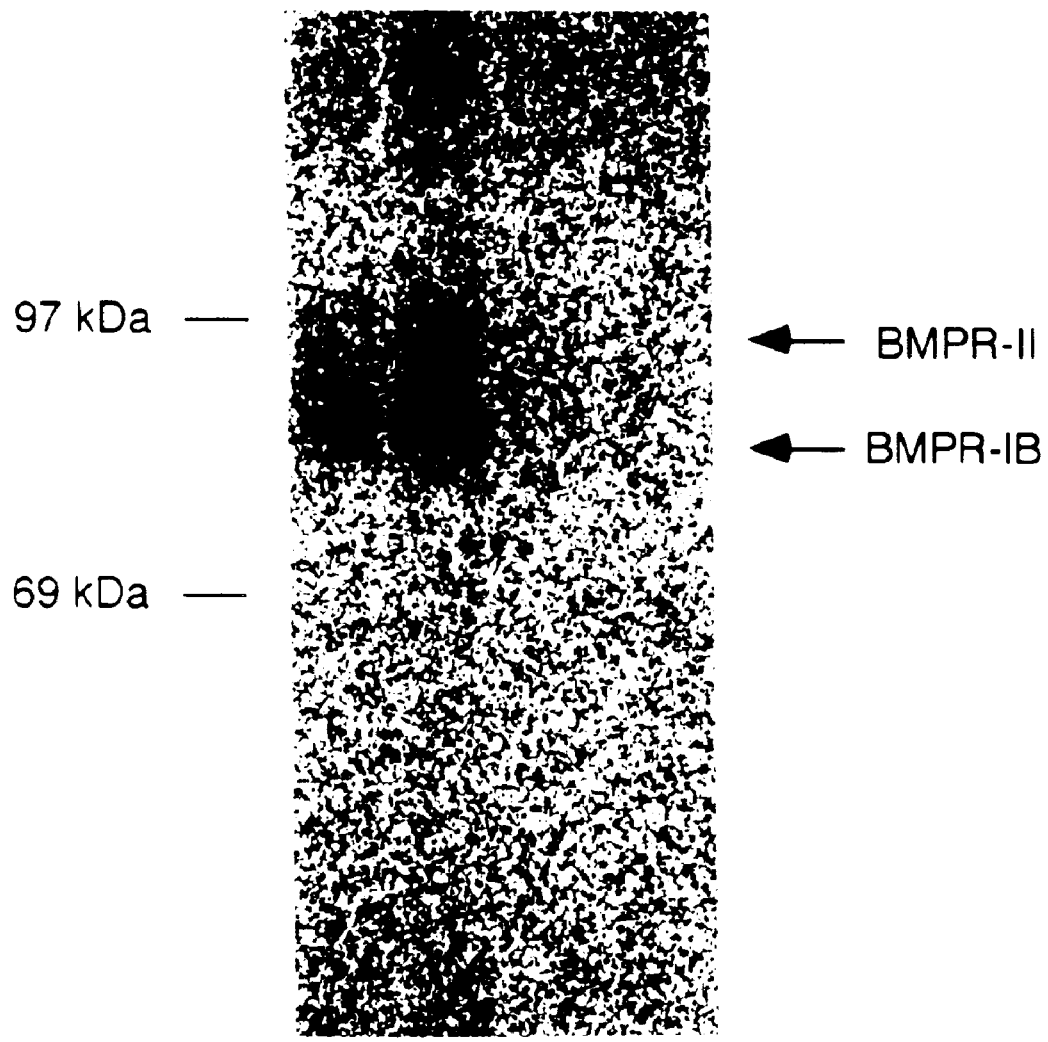

Similar results were obtained with the activin type IB receptor (ActR-IB) using $^{125}$I-activin A (FIG. 2B) and the BMP type IB receptor (BMPR-IB) using $^{125}$I-OP-1/BMP-7 (FIG. 2C) in which Smad6 bound to both wild type and kinase-defective type I receptors. These results suggest that Smad6 binds to the type I receptors in a ligand-dependent manner but exerts a role different from that of the other Smads.

Example 3

Effect of Smad6 on Phosphorylation of Smads

Smad2 is phosphorylated at its carboxy-terminal end by activated TβR-I (Macias-Silva et al., 1996). The phosphorylation is essential to the following downstream signaling events that culminate in transcriptional activation of the target genes, since disruption of the phosphorylation sites abrogated TGF-β-induced responses (Macias-Silva et al., 1996). Thus the effect of Smad6 on the phosphorylation of Smad2 was examined (FIG. 3). COS-7 cells were transiently transfected with constitutively active (TD) TβR-I, FLAG-Smad2 (F-Smad2), and/or Myc-Smad6 (M-Smad6). Cells were labeled with [$^{32}$P]orthophosphate and lysates were subjected to immunoprecipitation with anti-Myc antibody. Phosphorylated Smad6 was detected by SDS-PAGE and autoradiography. Doublet bands of phosphorylated Smad6 were detected. Cell lysates also were immunoprecipitated with anti-FLAG antibody to detect Smad2 phosphorylation. Expression levels of Smad6 (panel A), Smad2 and TβR-I (TD) (panel B) were monitored by labeling of the cells with [$^{35}$S]methionine/cysteine.

Figure 3A:
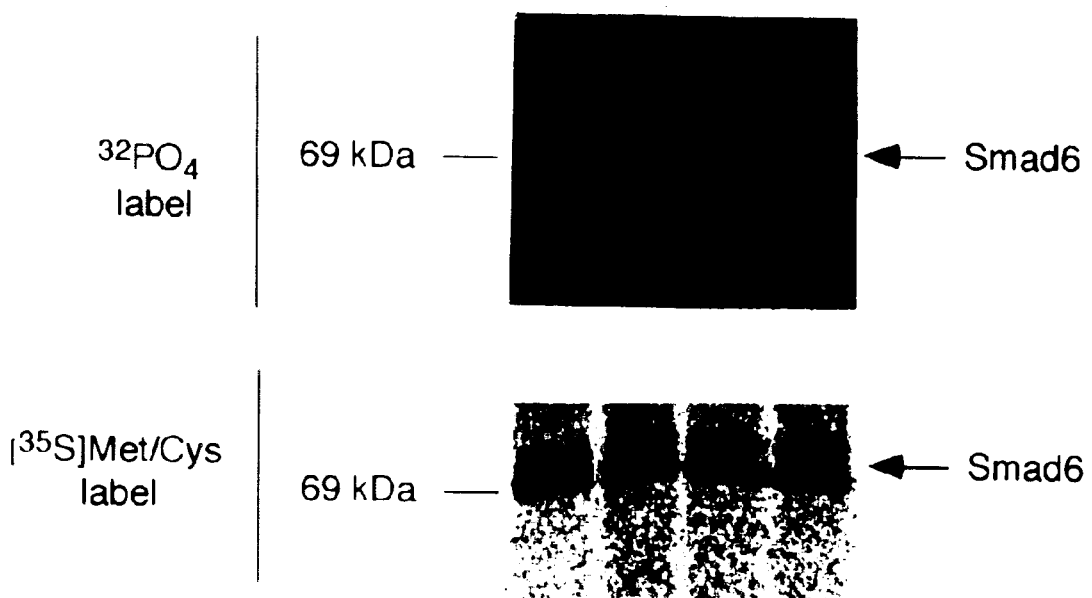
FIGS. 3A–3D are a representation of a photograph which demonstrates the effect of Smad6 on the phosphorylation of Smad1, Smad 2 and Smad3.
Figure 3B:
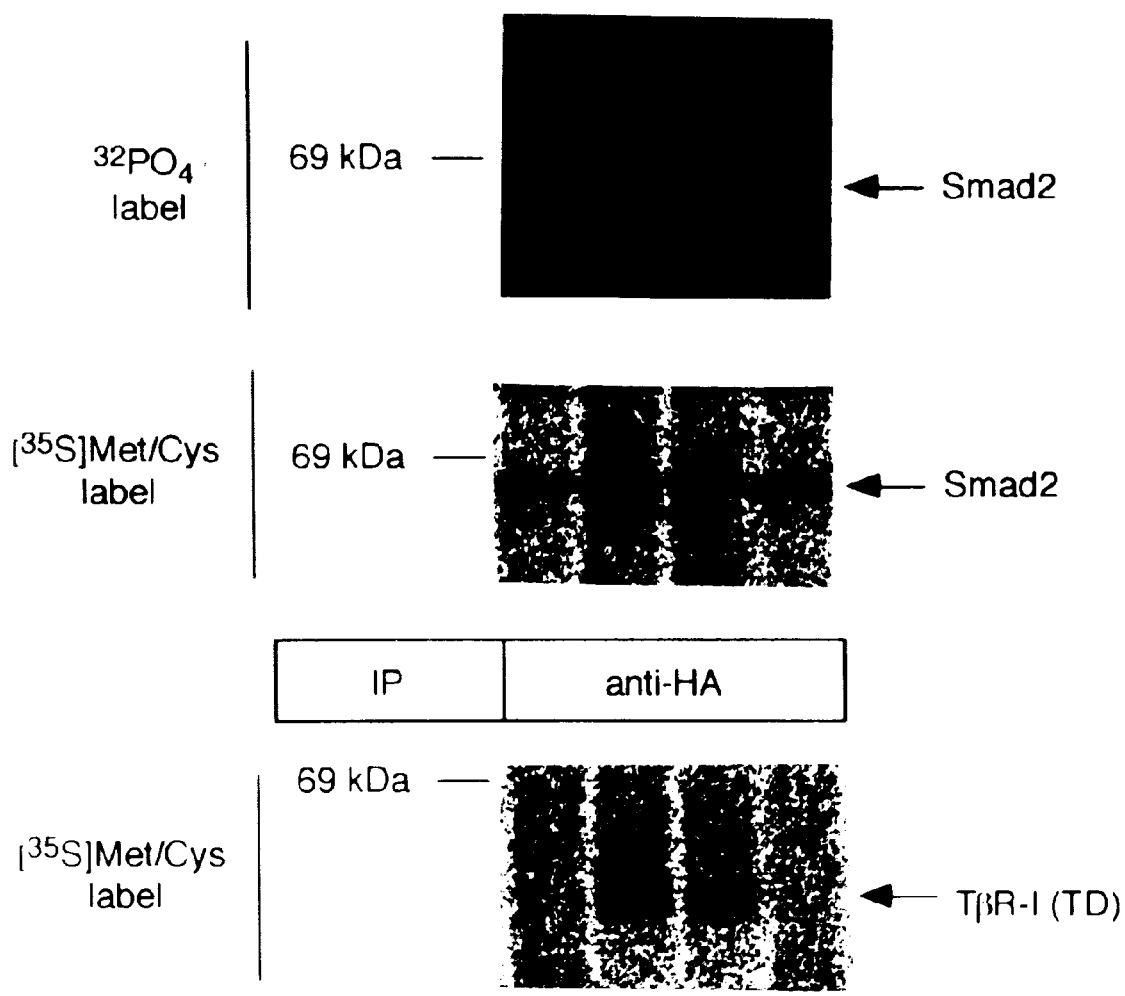

Neither TβR-I (TD) or FLAG-Smad2 affected the phosphorylation of Smad6. Phosphorylation of Smad2 induced by constitutively active TβR-I was suppressed by Smad6 (39% reduction as normalized for the $^{35}$S-labeled band), whereas Smad2 did not affect constitutive phosphorylation of Smad6 (FIGS. 3A, B).

Smad3 and Smad2 share 91% identity in their amino acid sequences and are independently shown to mediate TGF-β signals (Eppert et al. Cell 86:543–552, 1996; Zhang et al., 1996), although functional differences of the two molecules are still unknown. A similar experiment as above was done with Smad3. Smad6 rather enhanced receptor-induced phosphorylation of Smad3 (FIG. 3C), suggesting differential effects of Smad6 to these closely related molecules.

Figure 3C:
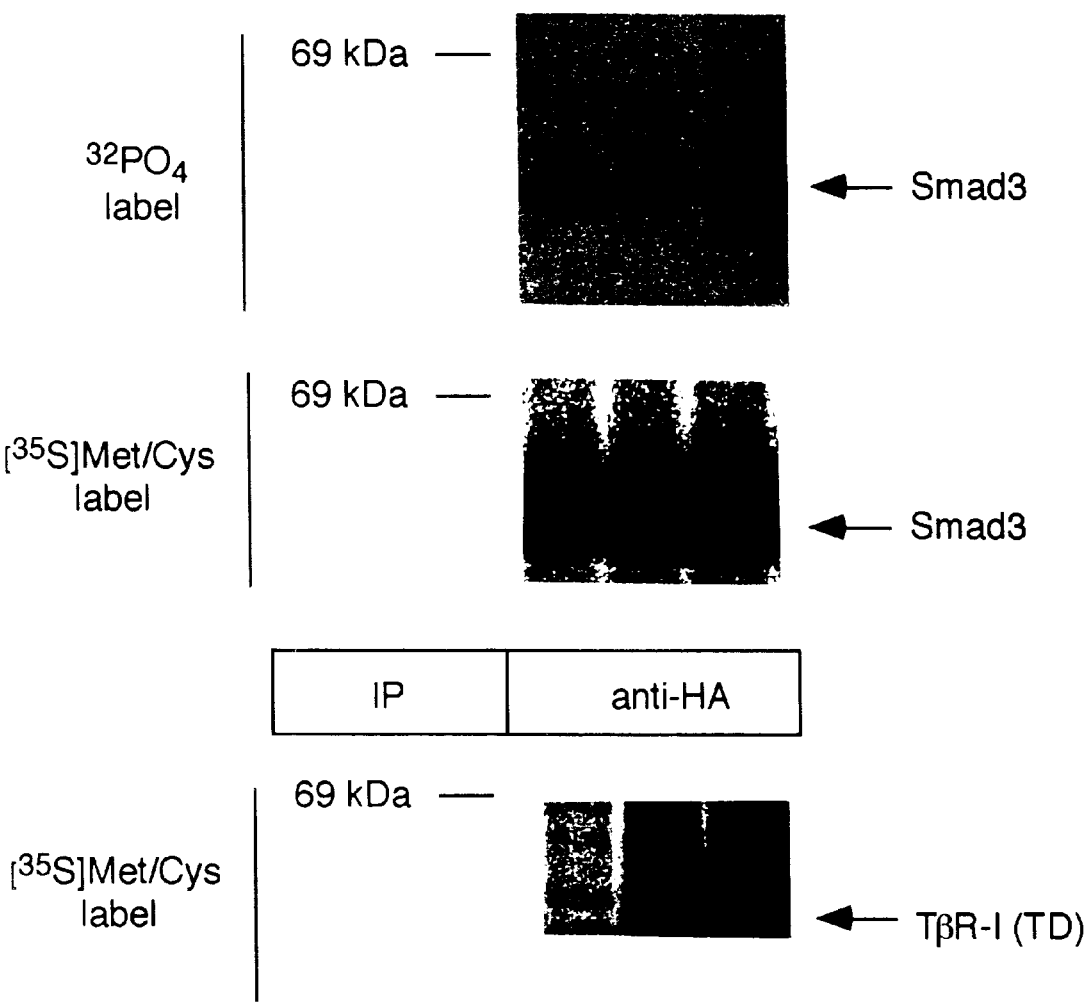
Figure 3D:
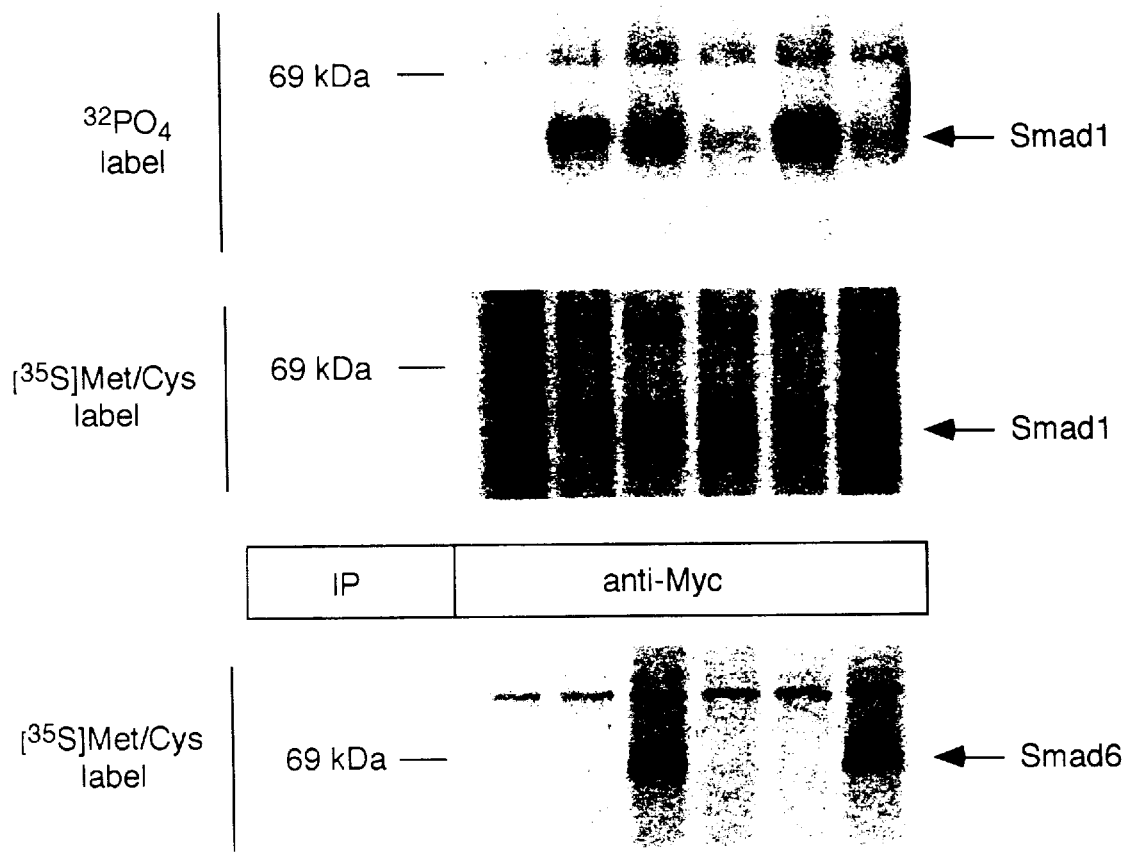

Next, the effect of Smad6 on Smad1phosphorylation was studied (FIG. 3D). Smad1was phosphorylated by the constitutively active BMP type IA receptor (BMPR-IA) as well as BMPR-IB. Smad6 efficiently inhibited phosphorylation induced by the latter (60% reduction) but not by the former. These results suggest that Smad6 acts as an inhibitor to certain members of the Smad family.

Example 4
Effect of Smad6 on Smad Complex Formation

Smad2 heteromerizes with Smad4 upon phosphorylation by TβR-I (Lagna et al., 1996). It was recently shown that TGF-β also induces association of Smad2 and Smad3 (Nakao et al., *EMBO. J.* 16:5353–5362, 1997). The effect of Smad6 on the heteromerization of these Smads was examined (FIG. 4). COS-7 cells were transfected with the indicated combination of plasmids and subjected to immunoprecipitation followed by Western blot detection. Expression levels of Smad2 (bottom), Smad4 (middle), and Smad6 (middle) were monitored. Note that Smad6 did not interact with Smad2 under these conditions (top).

Figure 4A:
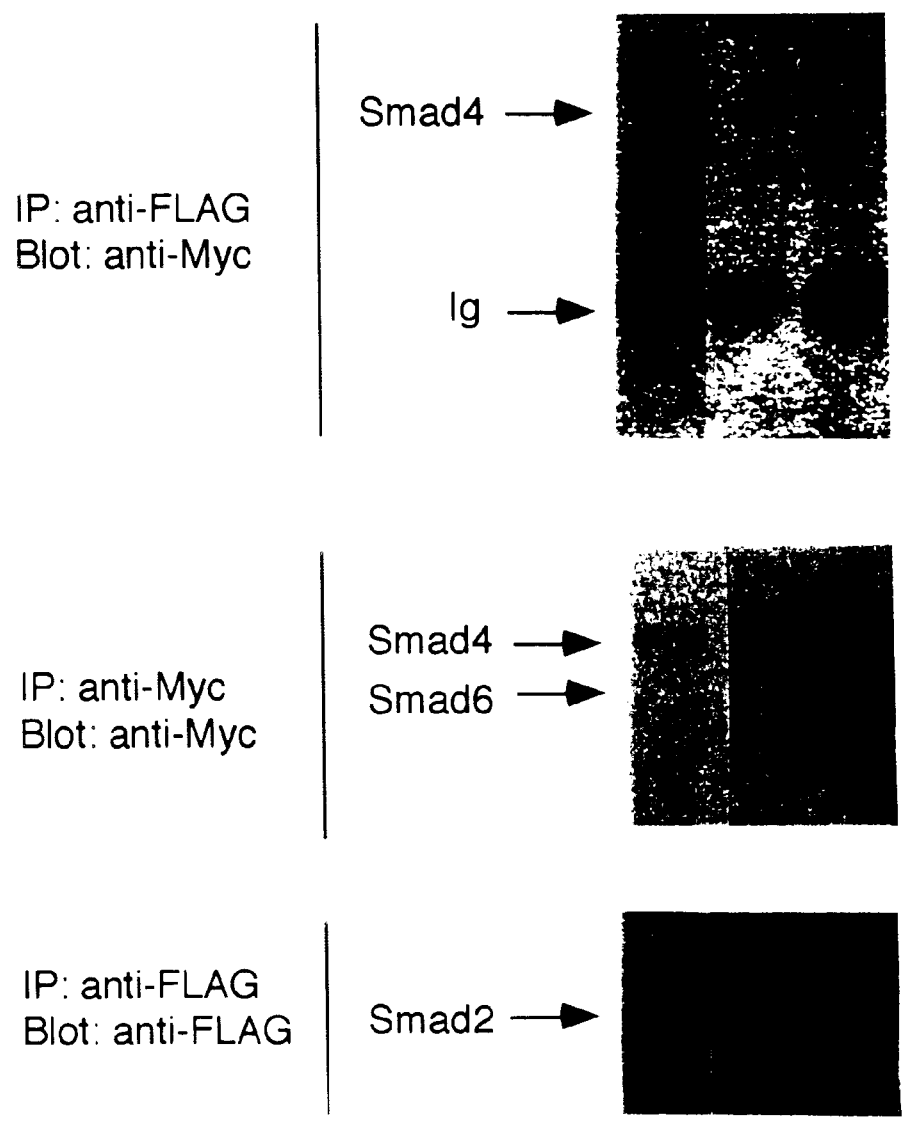

Smad2 formed a complex with Smad4 in the presence of constitutively active TβR-I as shown by coprecipitation of Smad4 with Smad2. The complex formation was abrogated by Smad6 (FIG. 4A, top panel). TβR-I-induced interaction of Smad3 and Smad4, however, was not affected by Smad6 (FIG. 4B), as Smad4 coprecipitated with Smad3 both in the presence and absence of Smad6 (top). This is consistent with the result that Smad6 does not inhibit Smad3 phosphorylation (FIG. 3C). Furthermore, heteromerization of Smad2 and Smad3 was inhibited by Smad6 (FIG. 4C), suggesting that phosphorylation of both proteins is necessary for this interaction. These results suggest that Smad6 specifically interferes with the activation of Smad2 in TGF-β signaling.

Example 5
Effect of Smad6 on TGF-β Signaling

The role of Smad6 in TGF-β signaling was tested, as assessed by luciferase reporter gene assays. P3TP-Lux, a sensitive reporter for TGF-β, was used in R mutant mink cells deficient in TβR-I (FIG. 5). Wild type TβR-I restored TGF-β response in these cells. Mink R mutant cells deficient in TβR-I were transfected with p3TP-Lux reporter, TβR-I, and increasing amounts (μg) of Smad6 DNA. Cells were treated with (closed bars) or without (open bars) 5 ng/ml TGF-β1 for 24 h. Smad6 suppressed the activation of the reporter gene in a dose-dependent manner (FIG. 5a). Transcriptional activation by constitutively active TβR-I was suppressed as well (FIG. 5b).

Cyclin A expression is necessary for cell cycle progression and is suppressed by TGF-β (Feng et al., *J. Biol. Chem.* 270:4237–24245, 1995). A cyclin A luciferase reporter, pCAL2, was used to examine the effect of Smad6 on TGF-β signaling. TβR-I (consitutively active) downregulated cyclin A luciferase activity, but increasing amounts of Smad6 counteracted the effects of TβR-I in the cyclin A luciferase assay (FIG. 5c). These results indicate that Smad6 interfered with TGF-β signals in two distinct responses.

Example 6
Regulation of Smad6 Expression by TGF-β1 and BMPs

Figure 6A:
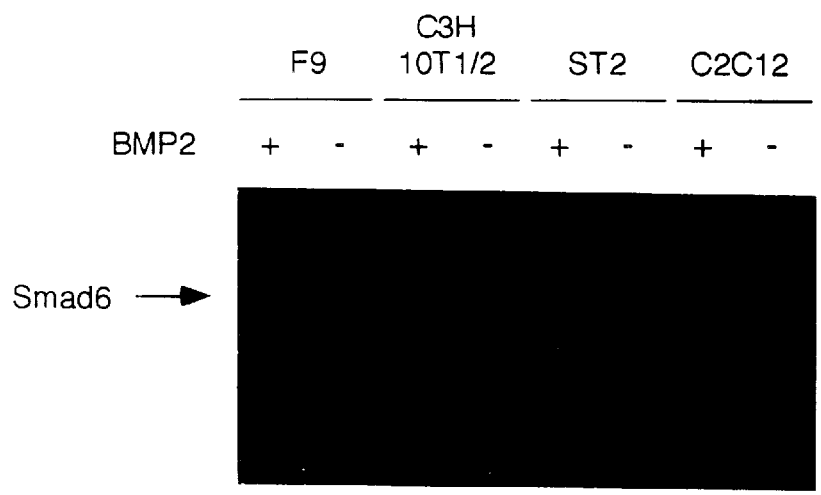
FIGS. 6A–6C are a representation of a photograph which shows the expression of Smad6 following stimulation of cells with BMP-2 (A), BMP-7/OP-1 (B) or TGF-β1 (C).

To determine the mechanisms by which the expression of Smad6 is controlled, the effect of TGF-β and other family members on Smad6 mRNA expression was examined. To determine the effect of BMP-2, BMP-2 was added at 300 ng/ml to the culture medium of several BMP-2-responsive cll lines: F9, C3H10T½, ST2 and C2C12. After 6 hours, poly $A^+$ mRNA was isolated from the cells as described above. Samples of mRNA were electrophoresed, blotted and probed with $^{32}P$-labeled Smad6 coding region. The results of the Northern blot are shown in FIG. 6A. Expression of Smad6 was induced in all of the BMP-2 responsive cell lines after BMP treatment.

Figure 6B:
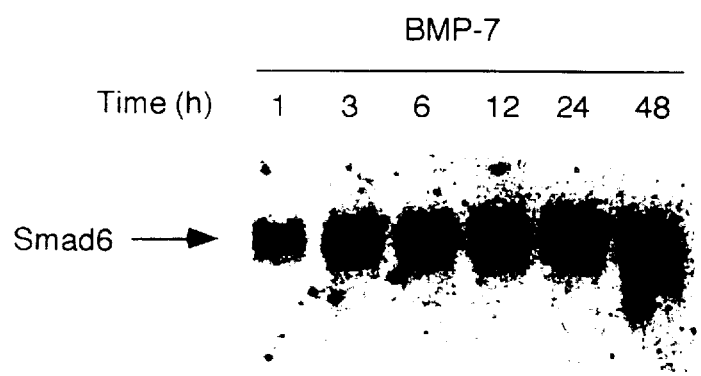

To determine the effect of OP-1/BMP-7, the expression of Smad6 mRNA in C2C12 myoblasts after stimulation with 300 ng/ml OP-1/BMP-7 was tested. Poly $A^+$ mRNA was isolated at the indicated times following OP-1/BMP-7 stimulation. As shown in FIG. 6B, Smad6 expression was induced by OP-1/BMP-7 at 6 hours after stimulation, and remained induced up to at least 48 hours after stimulation, the duration of the experiment.

Figure 6C:
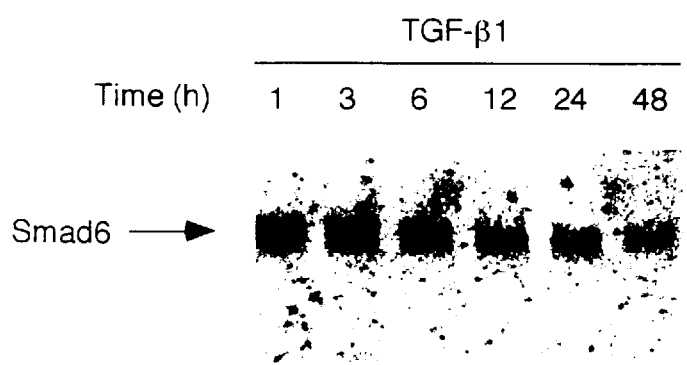

To determine the effect of TGF-β1, the expression of Smad6 mRNA in C2C12 myoblasts after stimulation with 25 ng/ml TGF-β1 was tested. Poly $A^+$ mRNA was isolated at the indicated times following TGF-β1 stimulation. As shown in FIG. 6C, Smad6 expression was induced by TGF-β1 at 1 hour after stimulation, but decreased thereafter. After 12 hours, the expression of Smad6 mRNA was below the basal level of expression.

In summary, the BMPs tested (BMP-2 and BMP-7/OP-1) induced the expression of Smad6 mRNA. In contrast, TGF-β1 initially induced the expression of Smad6, but Smad6 levels subsequently decreased to below basal levels. Thus different members of the TGF superfamily exert opposing effects on the expression of Smad6.

EQUIVALENTS

Those skilled in the art will recognize, or be able to ascertain using no more than routine experimentation, many equivalents to the specific embodiments of the invention described herein. Such equivalents are intended to be encompassed by the following claims. All references disclosed herein are incorporated by reference in their entirety.

What is claimed is:

1. An isolated polypeptide encoded by an isolated nucleic acid molecule selected from the group consisting of:

(a) nucleic acid molecules which hybridize under stringent conditions to a molecule consisting of the nucleic acid sequence of SEQ ID NO:1 and which code for a polypeptide which inhibits TGF-β superfamily signalling, provided that the nucleic acid molecules exclude sequences consisting only of SEQ ID NO:4, wherein the stringent conditions are selected from the group consisting of (1) hybridization at 65° C. in hybridization buffer (3.5×SSC, 0.02% Ficoll, 0.02% polyvinyl pyrrolidone, 0.02% Bovine Serum Albumin, 2.5 mM NaH$_2$PO$_4$(pH7), 0.5% SDS, 2 mM EDTA), wherein SSC is 0.15M sodium chloride/0.15M sodium citrate, pH7, SDS is sodium dodecyl sulphate, and EDTA is ethylenediaminetetracetic acid; and (2) hybridization at 65° C. in 5×SSC, 1% SDS, 5×Denhardt's solution and 10 μg/ml salmon sperm DNA, (b) nucleic acid molecules that differ from the nucleic acid molecules of (a) in codon sequence due to the degeneracy of the genetic code, and (c) complements of (a) and (b), wherein the polypeptide has a function selected from the group consisting of TGF-β superfamily signalling inhibitory activity, inhibition of TβR-I signaling, inhibition of ActR-I signaling, inhibition of BMPR-IB signaling, inhibition of Smad1 phosphorylation, inhibition of Smad2 phosphorylation, binding to TβR-I, binding to ActR-I and binding to BMPR-IB.

2. The isolated polypeptide of claim 1, wherein the isolated polypeptide consists of the amino acid sequence of SEQ ID NO:2.

3. An isolated polypeptide consisting of a functional fragment of the isolated polypeptide of claim 1, wherein the functional fragment has a function selected from the group consisting of inhibition of TβR-I signaling, inhibition of ActR-I signaling, inhibition of BMPR-IB signaling, inhibition of Smad1 phosphorylation, inhibition of Smad2 phosphorylation, binding to TβR-I, binding to ActR-I and binding to BMPR-IB.

4. The isolated polypeptide of claim 1, wherein the isolated polypeptide is encoded by an isolated nucleic acid molecule comprising the nucleotide sequence of SEQ ID NO:3.

5. The isolated nucleic acid molecule of claim 1, wherein the isolated polypeptide is encoded by an isolated nucleic acid molecule consisting of the nucleotide sequence of SEQ ID NO:3.

6. The isolated nucleic acid molecule of claim 1, wherein the isolated polypeptide is encoded by an isolated nucleic acid molecule comprising the nucleotide sequence of SEQ ID NO:1.

7. The isolated nucleic acid molecule of claim 1, wherein the isolated polypeptide is encoded by an isolated nucleic acid molecule consisting of the nucleotide sequence of SEQ ID NO:1.

8. An isolated polypeptide encoded by an isolated nucleic acid molecule selected from the group consisting of (a) a functional fragment of SEQ ID NO:3 between 20 and 1487 nucleotides in length, and (b) complements of (a), provided that the nucleic acid molecule includes a portion of SEQ ID NO:3 which is not overlapped by SEQ ID NO:4, wherein the functional fragment has a function selected from the group consisting of inhibition of TβR-I signaling, inhibition of ActR-I signaling, inhibition of BMPR-IB signaling, inhibition of Smad1 phosphorylation, inhibition of Smad2 phosphorylation, binding to TβR-I, binding to ActR-I and binding to BMPR-IB.

9. A composition comprising:

the polypeptide of claim 1, and a pharmaceutically acceptable carrier.

10. An isolated complex of polypeptides comprising:

a TGF-β superfamily receptor or receptor complex, bound to a polypeptide as claimed in claim 1.

11. The isolated complex of polypeptides of claim 10, wherein the polypeptide as claimed in claim 1 consists of the amino acid sequence of SEQ ID NO:2.

12. The isolated complex of claim 10, wherein the receptor or receptor complex is selected from the group consisting of TβRI, BMPR-IA, BMPR-IB, ActR-IA, a complex of TβRI and TβRII, a complex of BMPR-IA and BMPR-II, a complex of BMPR-IB and BMPR-II, a complex of ActR-IA and BMPR-II and a complex of ActR-IA and ActR-II.

* * * * *

SEQUENCE LISTING

<160> NUMBER OF SEQ ID NOS: 10

<210> SEQ ID NO 1
<211> LENGTH: 2534
<212> TYPE: DNA
<213> ORGANISM: Mus musculus
<220> FEATURE:
<221> NAME/KEY: CDS
<222> LOCATION: (751)..(2235)

<400> SEQUENCE: 1

```
ccctcgagg tcgacggtat cgataagctt gatatcgaat tccttttttt ttatggcttc      60
cactcatgtg ttgacaccg cgttcaggag agacttgccc caagtgcacc gagcgcccgg     120
```

```
                                                                -continued gacctgagac ggaattgctt ttcgtgcgtg caaaatccaa gcattttgag ttttgtttgg        180 gaccttttc ttgctttgct tttatttcta tttttatttt gttgcaggga tatgggagtt        240
atccacaagc cttagtttcg gatcctgcag ggaaagccca tgtagcatag cttggctttt       300
gaaggcagag ttgtgcagac acatttgggg gcacgacgca agcgctttgt gctcgtgtac       360
cagccgcgca acttttgaag gctcgccggc ccatgcaggg tgtctctagc atcgtttcgc       420
tggtggcttc cctaaggctc caaagcagct ggagttgagc ggtcccggcc atcgtgatc        480 catgtagccc gctggtccct cgcggactga ggctcaacac gcgcgtgttc ccggcccggc       540
ccggcccggc ttggcccggc gcgagctccc tcatgttgca gccctgcggt gcccttcga        600 cgacaggctg ttgcgcggtc tgcacggcgc ccgcggcag agcttcatgt ggggctgcgg        660
ccgctcagcc ggcgcctcgt tgaggsaacg gaccccggt aaccggagac cgcctcccct        720
cccaccahhh maggcgccaa aggtatcgt atg ttc agg tct aaa cgt tcg ggg        774
                                    Met Phe Arg Ser Lys Arg Ser Gly
                                      1               5 ctg gtg cga cga ctt tgg cga agt cgt gtg gtc cct gat cgg gag gaa        822
Leu Val Arg Arg Leu Trp Arg Ser Arg Val Val Pro Asp Arg Glu Glu
    10              15                  20 ggc agc ggc ggc ggc ggt ggt gtc gac gag gat ggg agc ctg ggc agc        870
Gly Ser Gly Gly Gly Gly Val Asp Glu Asp Gly Ser Leu Gly Ser
25              30                  35                  40 cga gct gag cct gcc ccg cgg gca cga gag ggc gga ggc tgc agc cgc        918
Arg Ala Glu Pro Ala Pro Arg Ala Arg Glu Gly Gly Gly Cys Ser Arg
                45                  50                  55 tcc gaa gtc cgc tcg gta gcc ccg cgg cgg ccc cgg gac gcg gtg gga        966
Ser Glu Val Arg Ser Val Ala Pro Arg Arg Pro Arg Asp Ala Val Gly
            60                  65                  70 ccg cga ggc gcc gcg atc gcg ggc agg cgc cgg cgc aca ggg ggc ctc       1014
Pro Arg Gly Ala Ala Ile Ala Gly Arg Arg Arg Thr Gly Gly Leu
        75                  80                  85 ccg agg ccc gtg tcg gag tcg ggg gcc ggg gct ggg ggc tcc ccg ctg       1062
Pro Arg Pro Val Ser Glu Ser Gly Ala Gly Ala Gly Gly Ser Pro Leu
    90                  95                  100 gat gtg gcg gag cct gga ggc cca ggc tgg ctg cct gag agt gac tgc       1110
Asp Val Ala Glu Pro Gly Gly Pro Gly Trp Leu Pro Glu Ser Asp Cys
105                 110                 115                 120 gag acg gtg acc tgc tgt ctc ttc tcc gaa cgg gac gca gca ggc gcg       1158
Glu Thr Val Thr Cys Cys Leu Phe Ser Glu Arg Asp Ala Ala Gly Ala
                125                 130                 135 ccc cgg gac tct ggc gat ccc caa gcc aga cag tcc ccg gag ccg gag       1206
Pro Arg Asp Ser Gly Asp Pro Gln Ala Arg Gln Ser Pro Glu Pro Glu
            140                 145                 150 gag ggc ggc ggg cct cgg agt cgc gaa gcc cgc tcg cga ctg ctg ctt       1254
Glu Gly Gly Gly Pro Arg Ser Arg Glu Ala Arg Ser Arg Leu Leu Leu
        155                 160                 165 ctg gag cag gag ctc aag acg gtc acg tac tcg ctg ctc aag agg ctc       1302
Leu Glu Gln Glu Leu Lys Thr Val Thr Tyr Ser Leu Leu Lys Arg Leu
    170                 175                 180 aag gag cgt tcg ctg gac acg ctg ttg gag gct gtg gag tcc cga ggc       1350
Lys Glu Arg Ser Leu Asp Thr Leu Leu Glu Ala Val Glu Ser Arg Gly
185                 190                 195                 200 ggc gta ccg ggc ggc tgc gtg ctg gtg ccg cgc gcc gac ctc cgc ttg       1398
Gly Val Pro Gly Gly Cys Val Leu Val Pro Arg Ala Asp Leu Arg Leu
                205                 210                 215 ggc ggc cag ccc gcg cca ccg cag ctg ctg ctc ggc cgc ctc ttc cgc       1446
Gly Gly Gln Pro Ala Pro Pro Gln Leu Leu Leu Gly Arg Leu Phe Arg
```

-continued

|  |  |  | 220 |  |  |  | 225 |  |  |  | 230 |  |  |  |  |
|---|---|---|---|---|---|---|---|---|---|---|---|---|---|---|---|
| tgg | cca | gac | ctg | cag | cac | gca | gtg | gag | ctg | aaa | ccc | ctg | tgc | ggc | tgc | 1494 |
| Trp | Pro | Asp | Leu | Gln | His | Ala | Val | Glu | Leu | Lys | Pro | Leu | Cys | Gly | Cys |  |
|  |  | 235 |  |  |  | 240 |  |  |  | 245 |  |  |  |  |  |

| cac | agc | ttt | acc | gcc | gcc | gcc | gac | ggg | ccc | acg | gtg | tgt | tgc | aac | ccc | 1542 |
| His | Ser | Phe | Thr | Ala | Ala | Ala | Asp | Gly | Pro | Thr | Val | Cys | Cys | Asn | Pro |  |
| 250 |  |  |  |  | 255 |  |  |  |  | 260 |  |  |  |  |  |  |

| tac | cac | ttc | agc | cgg | ctc | tgc | ggg | cca | gaa | tca | ccg | ccg | ccc | cct | tat | 1590 |
| Tyr | His | Phe | Ser | Arg | Leu | Cys | Gly | Pro | Glu | Ser | Pro | Pro | Pro | Pro | Tyr |  |
| 265 |  |  |  | 270 |  |  |  |  | 275 |  |  |  |  | 280 |  |  |

| tct | cgg | ctg | tct | cct | cct | gac | cag | tac | aag | cca | ctg | gat | ctg | tcc | gat | 1638 |
| Ser | Arg | Leu | Ser | Pro | Pro | Asp | Gln | Tyr | Lys | Pro | Leu | Asp | Leu | Ser | Asp |  |
|  |  |  |  | 285 |  |  |  | 290 |  |  |  |  | 295 |  |  |  |

| tct | aca | ttg | tct | tac | act | gaa | acc | gag | gcc | acc | aac | tcc | ctc | atc | act | 1686 |
| Ser | Thr | Leu | Ser | Tyr | Thr | Glu | Thr | Glu | Ala | Thr | Asn | Ser | Leu | Ile | Thr |  |
|  |  |  | 300 |  |  |  | 305 |  |  |  |  | 310 |  |  |  |  |

| gct | ccg | ggt | gaa | ttc | tca | gat | gcc | agc | atg | tct | ccg | gat | gcc | acc | aag | 1734 |
| Ala | Pro | Gly | Glu | Phe | Ser | Asp | Ala | Ser | Met | Ser | Pro | Asp | Ala | Thr | Lys |  |
|  |  | 315 |  |  |  | 320 |  |  |  | 325 |  |  |  |  |  |  |

| ccg | agc | cac | tgg | tgc | agc | gtg | gcg | tac | tgg | gag | cac | cgg | aca | cgc | gtg | 1782 |
| Pro | Ser | His | Trp | Cys | Ser | Val | Ala | Tyr | Trp | Glu | His | Arg | Thr | Arg | Val |  |
|  | 330 |  |  |  | 335 |  |  |  |  | 340 |  |  |  |  |  |  |

| ggc | cgc | ctc | tat | gcg | gtg | tac | gac | cag | gct | gtc | agc | att | ttc | tac | gac | 1830 |
| Gly | Arg | Leu | Tyr | Ala | Val | Tyr | Asp | Gln | Ala | Val | Ser | Ile | Phe | Tyr | Asp |  |
| 345 |  |  |  | 350 |  |  |  |  | 355 |  |  |  |  | 360 |  |  |

| cta | cct | cag | ggc | agc | ggc | ttc | tgc | ctg | ggc | cag | ctc | aac | ctg | gag | cag | 1878 |
| Leu | Pro | Gln | Gly | Ser | Gly | Phe | Cys | Leu | Gly | Gln | Leu | Asn | Leu | Glu | Gln |  |
|  |  |  |  | 365 |  |  |  |  | 370 |  |  |  |  | 375 |  |  |

| cgc | agt | gag | tcg | gtg | cgg | cgc | acg | cgc | agc | aag | atc | ggt | ttt | ggc | ata | 1926 |
| Arg | Ser | Glu | Ser | Val | Arg | Arg | Thr | Arg | Ser | Lys | Ile | Gly | Phe | Gly | Ile |  |
|  |  |  | 380 |  |  |  | 385 |  |  |  |  | 390 |  |  |  |  |

| ctg | ctc | agc | aag | gag | cca | gac | ggc | gtg | tgg | gcc | tac | aac | cgg | ggc | gag | 1974 |
| Leu | Leu | Ser | Lys | Glu | Pro | Asp | Gly | Val | Trp | Ala | Tyr | Asn | Arg | Gly | Glu |  |
|  |  | 395 |  |  |  | 400 |  |  |  | 405 |  |  |  |  |  |  |

| cac | ccc | atc | ttc | gtc | aac | tcc | ccg | acg | ctg | gat | gcg | ccc | gga | ggc | cgc | 2022 |
| His | Pro | Ile | Phe | Val | Asn | Ser | Pro | Thr | Leu | Asp | Ala | Pro | Gly | Gly | Arg |  |
|  | 410 |  |  |  | 415 |  |  |  |  | 420 |  |  |  |  |  |  |

| gcc | ctg | gtc | gtg | cgc | aag | gtg | cca | ccg | ggt | tac | tcc | atc | aag | gtg | ttc | 2070 |
| Ala | Leu | Val | Val | Arg | Lys | Val | Pro | Pro | Gly | Tyr | Ser | Ile | Lys | Val | Phe |  |
| 425 |  |  |  | 430 |  |  |  |  | 435 |  |  |  |  | 440 |  |  |

| gac | ttt | gag | cgc | tca | ggg | ctg | ctg | cag | cac | gca | gac | gcc | gct | cac | ggc | 2118 |
| Asp | Phe | Glu | Arg | Ser | Gly | Leu | Leu | Gln | His | Ala | Asp | Ala | Ala | His | Gly |  |
|  |  |  |  | 445 |  |  |  |  | 450 |  |  |  |  | 455 |  |  |

| ccc | tac | gac | ccg | cac | agt | gtg | cgc | atc | agc | ttc | gcc | aag | ggc | tgg | gga | 2166 |
| Pro | Tyr | Asp | Pro | His | Ser | Val | Arg | Ile | Ser | Phe | Ala | Lys | Gly | Trp | Gly |  |
|  |  |  | 460 |  |  |  | 465 |  |  |  |  | 470 |  |  |  |  |

| ccc | tgc | tac | tcg | cga | cag | ttc | atc | acc | tcc | tgc | ccc | tgt | tgg | ctg | gag | 2214 |
| Pro | Cys | Tyr | Ser | Arg | Gln | Phe | Ile | Thr | Ser | Cys | Pro | Cys | Trp | Leu | Glu |  |
|  |  | 475 |  |  |  |  | 480 |  |  |  |  | 485 |  |  |  |  |

| atc | cta | ctc | aac | aac | cac | aga | tagcaatgcg gctgccactg tgccgcagcg | 2265 |
| Ile | Leu | Leu | Asn | Asn | His | Arg |  |
|  | 490 |  |  |  | 495 |  |  |

| tccccccaacc | tctgggggc | cagcgcccag | agacaccacc | ccaggacaa | cctcgccctc | 2325 |
| cccccagata | tcatctacct | agatttaata | taaagtttta | tatattatat | ggaaatatat | 2385 |
| attatacttg | tggaattatg | gagtcatttt | tacaacgtaa | ttatttatat | atggtgcaat | 2445 |
| gtgtgtatat | ggagaaacaa | gaaagacgca | ctttggcttg | taattctttc | ggaattcctg | 2505 |
| cagcccgggg | gatccactag | ttctagagc |  |  |  | 2534 |

```
<210> SEQ ID NO 2
<211> LENGTH: 495
<212> TYPE: PRT
<213> ORGANISM: Mus musculus

<400> SEQUENCE: 2

Met Phe Arg Ser Lys Arg Ser Gly Leu Val Arg Leu Trp Arg Ser
1               5                   10                  15

Arg Val Val Pro Asp Arg Glu Glu Gly Ser Gly Gly Gly Gly Val
                20                  25                  30

Asp Glu Asp Gly Ser Leu Gly Ser Arg Ala Glu Pro Ala Pro Arg Ala
                35                  40                  45

Arg Glu Gly Gly Gly Cys Ser Arg Ser Glu Val Arg Ser Val Ala Pro
    50                  55                  60

Arg Arg Pro Arg Asp Ala Val Gly Pro Arg Gly Ala Ala Ile Ala Gly
65                  70                      75                  80

Arg Arg Arg Arg Thr Gly Gly Leu Pro Arg Pro Val Ser Glu Ser Gly
                85                  90                  95

Ala Gly Ala Gly Gly Ser Pro Leu Asp Val Ala Glu Pro Gly Gly Pro
                100                 105                 110

Gly Trp Leu Pro Glu Ser Asp Cys Glu Thr Val Thr Cys Cys Leu Phe
            115                 120                 125

Ser Glu Arg Asp Ala Ala Gly Ala Pro Arg Asp Ser Gly Asp Pro Gln
130                 135                 140

Ala Arg Gln Ser Pro Glu Pro Glu Gly Gly Gly Pro Arg Ser Arg
145                 150                 155                 160

Glu Ala Arg Ser Arg Leu Leu Leu Leu Glu Gln Glu Leu Lys Thr Val
                165                 170                 175

Thr Tyr Ser Leu Leu Lys Arg Leu Lys Glu Arg Ser Leu Asp Thr Leu
                180                 185                 190

Leu Glu Ala Val Glu Ser Arg Gly Gly Val Pro Gly Gly Cys Val Leu
                195                 200                 205

Val Pro Arg Ala Asp Leu Arg Leu Gly Gly Gln Pro Ala Pro Pro Gln
210                 215                 220

Leu Leu Leu Gly Arg Leu Phe Arg Trp Pro Asp Leu Gln His Ala Val
225                 230                 235                 240

Glu Leu Lys Pro Leu Cys Gly Cys His Ser Phe Thr Ala Ala Ala Asp
                245                 250                 255

Gly Pro Thr Val Cys Cys Asn Pro Tyr His Phe Ser Arg Leu Cys Gly
            260                 265                 270

Pro Glu Ser Pro Pro Pro Tyr Ser Arg Leu Ser Pro Asp Gln
                275                 280                 285

Tyr Lys Pro Leu Asp Leu Ser Asp Ser Thr Leu Ser Tyr Thr Glu Thr
    290                 295                 300

Glu Ala Thr Asn Ser Leu Ile Thr Ala Pro Gly Glu Phe Ser Asp Ala
305                 310                 315                 320

Ser Met Ser Pro Asp Ala Thr Lys Pro Ser His Trp Cys Ser Val Ala
                325                 330                 335

Tyr Trp Glu His Arg Thr Arg Val Gly Arg Leu Tyr Ala Val Tyr Asp
                340                 345                 350

Gln Ala Val Ser Ile Phe Tyr Asp Leu Pro Gln Gly Ser Gly Phe Cys
                355                 360                 365

Leu Gly Gln Leu Asn Leu Glu Gln Arg Ser Glu Ser Val Arg Arg Thr
```

```
                370                 375                 380
Arg Ser Lys Ile Gly Phe Gly Ile Leu Leu Ser Lys Glu Pro Asp Gly
385                 390                 395                 400

Val Trp Ala Tyr Asn Arg Gly Glu His Pro Ile Phe Val Asn Ser Pro
                405                 410                 415

Thr Leu Asp Ala Pro Gly Gly Arg Ala Leu Val Val Arg Lys Val Pro
            420                 425                 430

Pro Gly Tyr Ser Ile Lys Val Phe Asp Phe Glu Arg Ser Gly Leu Leu
        435                 440                 445

Gln His Ala Asp Ala Ala His Gly Pro Tyr Asp Pro His Ser Val Arg
    450                 455                 460

Ile Ser Phe Ala Lys Gly Trp Gly Pro Cys Tyr Ser Arg Gln Phe Ile
465                 470                 475                 480

Thr Ser Cys Pro Cys Trp Leu Glu Ile Leu Leu Asn Asn His Arg
                485                 490                 495

<210> SEQ ID NO 3
<211> LENGTH: 1488
<212> TYPE: DNA
<213> ORGANISM: Mus musculus

<400> SEQUENCE: 3
atgttcaggt ctaaacgttc ggggctggtg cgacgacttt ggcgaagtcg tgtggtccct     60
gatcgggagg aaggcagcgg cggcggcggt ggtgtcgacg aggatgggag cctgggcagc    120
cgagctgagc ctgccccgcg ggcacgagag ggcggaggct gcagccgctc cgaagtccgc    180
tcggtagccc cgcggcggcc ccgggacgcg gtgggaccgc gaggcgccgc gatcgcgggc    240
aggcgccggc gcacagggg cctcccgagg cccgtgtcgg agtcggggc cggggctggg     300 ggctccccgc tggatgtggc ggagcctgga ggcccaggct ggctgcctga gagtgactgc    360
gagacggtga cctgctgtct cttctccgaa cgggacgcag caggcgcgcc ccgggactct    420
ggcgatcccc aagccagaca gtccccggag ccggaggagg gcggcgggcc tcggagtcgc    480
gaagcccgct cgcgactgct gcttctggag caggagctca agacggtcac gtactcgctg    540
ctcaagaggc tcaaggagcg ttcgctggac acgctgttgg aggctgtgga gtcccgaggc    600
ggcgtaccgg gcggctgcgt gctggtgccg cgcgccgacc tccgcttggg cggccagccc    660
gcgccaccgc agctgctgct cggccgcctc ttccgctggc cagacctgca gcacgcagtg    720
gagctgaaaa ccctgtgcgg ctgccacagc tttaccgccg ccgccgacgg gcccacggtg    780
tgttgcaacc cctaccactt cagccggctc tgcgggccag aatcaccgcc gcccccctat    840
tctcggctgt ctcctcctga ccagtacaag ccactggatc tgtccgattc acattgtct    900 tacactgaaa ccgaggccac caactccctc atcactgctc cgggtgartt ctcagatgcc    960
agcatgtctc cggatgccac caagccgagc cactggtgca gcgtggcgta ctgggagcac   1020
cggacacgcg tgggccgcct ctatgcggtg tacgaccagg ctgtcagcat tttctacgac   1080
ctacctcagg gcagcggctt ctgcctgggc cagctcaacc tggagcagcg cagtgagtcg   1140
gtgcggcgca cgcgcagcaa gatcggtttt ggcatactgc tcagcaagga ccagacggc   1200 gtgtgggcct acaaccgggg cgagcacccc atcttcgtca actccccgac gctggatgcg   1260
cccggaggcc gcgccctggt cgtgcgcaag gtgccaccgg ttactccat caaggtgttc   1320 gactttgagc gctcagggct gctgcagcac gcagacgccg ctcacggccc ctacgacccg   1380
cacagtgtgc gcatcagctt cgccaagggc tggggaccct gctactcgcg acagttcatc   1440
```

-continued acctcctgcc cctgttggct ggagatccta ctcaacaacc acagatag                    1488

<210> SEQ ID NO 4
<211> LENGTH: 1280
<212> TYPE: DNA
<213> ORGANISM: Homo sapiens

<400> SEQUENCE: 4
aaaagaacga atccagcacc aaaacgtgct acaacatgga tgaacttcga tgactttgtg      60
ccacatgaaa aagaagcca gccacaaaag gccatatatt gtatgaaatg aaatgtccag      120
aatgggcaaa cccatagaga cacaaaaatc tccgccacct ccctactctc ggctgtctcc    180
tcgcgacgag tacaagccac tggatctgtc cgattccaca ttgtcttaca ctgaaacgga    240
ggctaccaac tccctcatca ctgctccggg tgaattctca gacgccagca tgtctccgga    300
cgccaccaag ccgagccact ggtgcagcgt ggcgtactgg gagcaccgga cgcgcgtggg    360
ccgcctctat gcggtgtacg accaggccgt cagcatcttc tacgacctac ctcagggcag    420
cggcttctgc ctgggccagc tcaacctgga gcagcgcagc gagtcggtgc ggcgaacgcg    480
cagcaagatc ggcttcggca tcctgctcag caaggagccc gacggcgtgt gggcctacaa    540
ccgcggcgag cacccatct cgtcaactc cccgacgctg gacgcgcccg gcggccgcgc      600
cctggtcgtg cgcaaggtgc ccccggcta ctccatcaag gtgttcgact cgagcgctc     660
gggcctgcag cacgcgcccg agcccgacgc cgccgacggc ccctacgacc ccaacagcgt    720
ccgcatcagc ttcgccaagg gctgggggcc ctgctactcc cggcagttca tcacctcctg    780
cccctgctgg ctggagatcc tcctcaacaa ccccagatag tggcggcccc ggcgggaggg    840
gcgggtggga ggccgcggcc accgccacct gccggcctcg agaggggccg atgcccagag    900
acacagcccc cacggacaaa acccccaga tatcatctac ctagatttaa tataaagttt     960
tatatattat atggaaatat atattatact tgtaattatg gagtcatttt tacaatgtaa   1020
ttatttatgt atggtgcaat gtgtgtatat ggacaaaaca agaaagacgc actttggctt   1080
ataattcttt caatacagat atattttctt tctcttcctc cttcctcttc cttactttt    1140
atatatatat ataagaaaa tgatacagca gagctaggtg gaaaagcctg ggtttggtgt    1200
atggttttg agatattaat gcccagacaa aaagctaata ccagtcactc gataataaag    1260
tattcgcatt ataaaaaaga                                                1280

<210> SEQ ID NO 5
<211> LENGTH: 235
<212> TYPE: PRT
<213> ORGANISM: Homo sapiens

<400> SEQUENCE: 5

Met Ser Arg Met Gly Lys Pro Ile Glu Thr Gln Lys Ser Pro Pro
1               5                   10                  15

Pro Tyr Ser Arg Leu Ser Pro Arg Asp Glu Tyr Lys Pro Leu Asp Leu
            20                  25                  30

Ser Asp Ser Thr Leu Ser Tyr Thr Glu Thr Glu Ala Thr Asn Ser Leu
        35                  40                  45

Ile Thr Ala Pro Gly Glu Phe Ser Asp Ala Ser Met Ser Pro Asp Ala
    50                  55                  60

Thr Lys Pro Ser His Trp Cys Ser Val Ala Tyr Trp Glu His Arg Thr
65                  70                  75                  80

Arg Val Gly Arg Leu Tyr Ala Val Tyr Asp Gln Ala Val Ser Ile Phe
                85                  90                  95

```
Tyr Asp Leu Pro Gln Gly Ser Gly Phe Cys Leu Gly Gln Leu Asn Leu
            100                 105                 110

Glu Gln Arg Ser Glu Ser Val Arg Arg Thr Arg Ser Lys Ile Gly Phe
        115                 120                 125

Gly Ile Leu Leu Ser Lys Glu Pro Asp Gly Val Trp Ala Tyr Asn Arg
130                 135                 140

Gly Glu His Pro Ile Phe Val Asn Ser Pro Thr Leu Asp Ala Pro Gly
145                 150                 155                 160

Gly Arg Ala Leu Val Val Arg Lys Val Pro Pro Gly Tyr Ser Ile Lys
                165                 170                 175

Val Phe Asp Phe Glu Arg Ser Gly Leu Gln His Ala Pro Glu Pro Asp
                180                 185                 190

Ala Ala Asp Gly Pro Tyr Asp Pro Asn Ser Val Arg Ile Ser Phe Ala
            195                 200                 205

Lys Gly Trp Gly Pro Cys Tyr Ser Arg Gln Phe Ile Thr Ser Cys Pro
        210                 215                 220

Cys Trp Leu Glu Ile Leu Leu Asn Asn Pro Arg
225                 230                 235

<210> SEQ ID NO 6
<211> LENGTH: 465
<212> TYPE: PRT
<213> ORGANISM: Homo sapiens

<400> SEQUENCE: 6

Met Asn Val Thr Ser Leu Phe Ser Phe Thr Ser Pro Ala Val Lys Arg
1               5                   10                  15

Leu Leu Gly Trp Lys Gln Gly Asp Glu Glu Lys Trp Ala Glu Lys
            20                  25                  30

Ala Val Asp Ala Leu Val Lys Lys Leu Lys Lys Lys Gly Ala Met
            35                  40                  45

Glu Glu Leu Glu Lys Ala Leu Ser Cys Pro Gly Gln Pro Ser Asn Cys
50                  55                  60

Val Thr Ile Pro Arg Ser Leu Asp Gly Arg Leu Gln Val Ser His Arg
65                  70                  75                  80

Lys Gly Leu Pro His Val Ile Tyr Cys Arg Val Trp Arg Trp Pro Asp
                85                  90                  95

Leu Gln Ser His His Glu Leu Lys Pro Leu Glu Cys Cys Glu Phe Pro
            100                 105                 110

Phe Gly Ser Lys Gln Lys Glu Val Cys Ile Asn Pro Tyr His Tyr Lys
        115                 120                 125

Arg Val Glu Ser Pro Val Leu Pro Pro Val Leu Val Pro Arg His Ser
130                 135                 140

Glu Tyr Asn Pro Gln His Ser Leu Leu Ala Gln Phe Arg Asn Leu Gly
145                 150                 155                 160

Gln Asn Glu Pro His Met Pro Leu Asn Ala Thr Phe Pro Asp Ser Phe
                165                 170                 175

Gln Gln Pro Asn Ser His Pro Phe Pro His Ser Pro Asn Ser Ser Tyr
            180                 185                 190

Pro Asn Ser Pro Gly Ser Ser Ser Thr Tyr Pro His Ser Pro Thr
        195                 200                 205

Ser Ser Asp Pro Gly Ser Pro Phe Gln Met Pro Ala Asp Thr Pro Pro
        210                 215                 220

Pro Ala Tyr Leu Pro Pro Glu Asp Pro Met Thr Gln Asp Gly Ser Gln
```

```
                225                 230                 235                 240
Pro Met Asp Thr Asn Met Met Ala Pro Pro Leu Pro Ser Glu Ile Asn
                    245                 250                 255

Arg Gly Asp Val Gln Ala Val Ala Tyr Glu Glu Pro Lys His Trp Cys
                260                 265                 270

Ser Ile Val Tyr Tyr Glu Leu Asn Asn Arg Val Gly Glu Ala Phe His
                275                 280                 285

Ala Ser Ser Thr Ser Val Leu Val Asp Gly Phe Thr Asp Pro Ser Asn
            290                 295                 300

Asn Lys Asn Arg Phe Cys Leu Gly Leu Leu Ser Asn Val Asn Arg Asn
305                 310                 315                 320

Ser Thr Ile Glu Asn Thr Arg Arg His Ile Gly Lys Gly Val His Leu
                325                 330                 335

Tyr Tyr Val Gly Gly Glu Val Tyr Ala Glu Cys Leu Ser Asp Ser Ser
                340                 345                 350

Ile Phe Val Gln Ser Arg Asn Cys Asn Tyr His His Gly Phe His Pro
            355                 360                 365

Thr Thr Val Cys Lys Ile Pro Ser Gly Cys Ser Leu Lys Ile Phe Asn
        370                 375                 380

Asn Gln Glu Phe Ala Gln Leu Leu Ala Gln Ser Val Asn His Gly Phe
385                 390                 395                 400

Glu Thr Val Tyr Glu Leu Thr Lys Met Cys Thr Ile Arg Met Ser Phe
                405                 410                 415

Val Lys Gly Trp Gly Ala Glu Tyr His Arg Gln Asp Val Thr Ser Thr
            420                 425                 430

Pro Cys Trp Ile Glu Ile His Leu His Gly Pro Leu Gln Trp Leu Asp
        435                 440                 445

Lys Val Leu Thr Gln Met Gly Ser Pro His Asn Pro Ile Ser Ser Val
    450                 455                 460

Ser
465

<210> SEQ ID NO 7
<211> LENGTH: 467
<212> TYPE: PRT
<213> ORGANISM: Homo sapiens

<400> SEQUENCE: 7

Met Ser Ser Ile Leu Pro Phe Thr Pro Pro Val Val Lys Arg Leu Leu
1               5                   10                  15

Gly Trp Lys Lys Ser Ala Gly Gly Ser Gly Ala Gly Gly Gly Gly Glu
                20                  25                  30

Gln Asn Gly Gln Glu Glu Lys Trp Cys Gln Lys Ala Val Lys Ser Leu
            35                  40                  45

Val Lys Lys Leu Lys Lys Thr Gly Arg Leu Asp Glu Leu Glu Lys Ala
        50                  55                  60

Ile Thr Thr Gln Asn Cys Asn Thr Lys Cys Val Thr Ile Pro Ser Thr
65                  70                  75                  80

Cys Ser Glu Ile Trp Gly Leu Ser Thr Ala Asn Thr Val Asp Gln Trp
                85                  90                  95

Asp Thr Thr Gly Leu Tyr Ser Phe Ser Glu Gln Thr Arg Ser Leu Asp
            100                 105                 110

Gly Arg Leu Gln Val Ser His Arg Lys Gly Leu Pro His Val Ile Tyr
        115                 120                 125
```

```
Cys Arg Leu Trp Arg Trp Pro Asp Leu His Ser His His Glu Leu Lys
        130                 135                 140

Ala Ile Glu Asn Cys Glu Tyr Ala Phe Asn Leu Lys Lys Asp Glu Val
145                 150                 155                 160

Cys Val Asn Pro Tyr His Tyr Gln Arg Val Glu Thr Pro Val Leu Pro
                165                 170                 175

Pro Val Leu Val Pro Arg His Thr Glu Ile Leu Thr Glu Leu Pro Pro
            180                 185                 190

Leu Asp Asp Tyr Thr His Ser Ile Pro Glu Asn Thr Asn Phe Pro Ala
                195                 200                 205

Gly Ile Glu Pro Gln Ser Asn Tyr Ile Pro Glu Thr Pro Pro Pro Gly
        210                 215                 220

Tyr Ile Ser Glu Asp Gly Glu Thr Ser Asp Gln Gln Leu Asn Gln Ser
225                 230                 235                 240

Met Asp Thr Gly Ser Pro Ala Glu Leu Ser Pro Thr Thr Leu Ser Pro
                245                 250                 255

Val Asn His Ser Leu Asp Leu Gln Pro Val Thr Tyr Ser Glu Pro Ala
            260                 265                 270

Phe Trp Cys Ser Ile Ala Tyr Tyr Glu Leu Asn Gln Arg Val Gly Glu
        275                 280                 285

Thr Phe His Ala Ser Gln Pro Ser Leu Thr Val Asp Gly Phe Thr Asp
        290                 295                 300

Pro Ser Asn Ser Glu Arg Phe Cys Leu Gly Leu Leu Ser Asn Val Asn
305                 310                 315                 320

Arg Asn Ala Thr Val Glu Met Thr Arg Arg His Ile Gly Arg Gly Val
                325                 330                 335

Arg Leu Tyr Tyr Ile Gly Gly Glu Val Phe Ala Glu Cys Leu Ser Asp
            340                 345                 350

Ser Ala Ile Phe Val Gln Ser Pro Asn Cys Asn Gln Arg Tyr Gly Trp
        355                 360                 365

His Pro Ala Thr Val Cys Lys Ile Pro Pro Gly Cys Asn Leu Lys Ile
    370                 375                 380

Phe Asn Asn Gln Glu Phe Ala Ala Leu Leu Ala Gln Ser Val Asn Gln
385                 390                 395                 400

Gly Phe Glu Ala Val Tyr Gln Leu Thr Arg Met Cys Thr Ile Arg Met
                405                 410                 415

Ser Phe Val Lys Gly Trp Gly Ala Glu Tyr Arg Arg Gln Thr Val Thr
            420                 425                 430

Ser Thr Pro Cys Trp Ile Glu Leu His Leu Asn Gly Pro Leu Gln Trp
        435                 440                 445

Leu Asp Lys Val Leu Thr Gln Met Gly Ser Pro Ser Val Arg Cys Ser
    450                 455                 460

Ser Met Ser
465

<210> SEQ ID NO 8
<211> LENGTH: 425
<212> TYPE: PRT
<213> ORGANISM: Homo sapiens

<400> SEQUENCE: 8

Met Ser Ser Ile Leu Pro Phe Thr Pro Pro Ile Val Lys Arg Leu Leu
1               5                   10                  15

Gly Trp Lys Lys Gly Glu Gln Asn Gly Gln Glu Glu Lys Trp Cys Glu
            20                  25                  30
```

```
Lys Ala Val Lys Ser Leu Val Lys Leu Lys Lys Thr Gly Gln Leu
             35                  40                  45
Asp Glu Leu Glu Lys Ala Ile Thr Thr Gln Asn Val Asn Thr Lys Cys
 50                  55                  60
Ile Thr Ile Pro Arg Ser Leu Asp Gly Arg Leu Gln Val Ser His Arg
 65                  70                  75                  80
Lys Gly Leu Pro His Val Ile Tyr Cys Arg Leu Trp Arg Trp Pro Asp
                 85                  90                  95
Leu His Ser His His Glu Leu Arg Ala Met Glu Leu Cys Glu Phe Ala
            100                 105                 110
Phe Asn Met Lys Lys Asp Glu Val Cys Val Asn Pro Tyr His Tyr Gln
            115                 120                 125
Arg Val Glu Thr Pro Val Leu Pro Pro Val Leu Val Pro Arg His Thr
            130                 135                 140
Glu Ile Pro Ala Glu Phe Pro Pro Leu Asp Asp Tyr Ser His Ser Ile
145                 150                 155                 160
Pro Glu Asn Thr Asn Phe Pro Ala Gly Ile Glu Pro Gln Ser Asn Ile
                165                 170                 175
Pro Glu Thr Pro Pro Pro Gly Tyr Leu Ser Glu Asp Gly Glu Thr Ser
            180                 185                 190
Asp His Gln Met Asn His Ser Met Asp Ala Gly Ser Pro Asn Leu Ser
            195                 200                 205
Pro Asn Pro Met Ser Pro Ala His Asn Asn Leu Asp Leu Gln Pro Val
            210                 215                 220
Thr Tyr Cys Glu Pro Ala Phe Trp Cys Ser Ile Ser Tyr Tyr Glu Leu
225                 230                 235                 240
Asn Gln Arg Val Gly Glu Thr Phe His Ala Ser Gln Pro Ser Met Thr
                245                 250                 255
Val Asp Gly Phe Thr Asp Pro Ser Asn Ser Glu Arg Phe Cys Leu Gly
            260                 265                 270
Leu Leu Ser Asn Val Asn Arg Asn Ala Ala Val Glu Leu Thr Arg Arg
            275                 280                 285
His Ile Gly Arg Gly Val Arg Leu Tyr Tyr Ile Gly Gly Glu Val Phe
            290                 295                 300
Ala Glu Cys Leu Ser Asp Ser Ala Ile Phe Val Gln Ser Pro Asn Cys
305                 310                 315                 320
Asn Gln Arg Tyr Gly Trp His Pro Ala Thr Val Cys Lys Ile Pro Pro
                325                 330                 335
Gly Cys Asn Leu Lys Ile Phe Asn Asn Gln Glu Phe Ala Ala Leu Leu
            340                 345                 350
Ala Gln Ser Val Asn Gln Gly Phe Glu Ala Val Tyr Gln Leu Thr Arg
            355                 360                 365
Met Cys Thr Ile Arg Met Ser Phe Val Lys Gly Trp Gly Ala Glu Tyr
            370                 375                 380
Arg Arg Gln Thr Val Thr Ser Thr Pro Cys Trp Ile Glu Leu His Leu
385                 390                 395                 400
Asn Gly Pro Leu Gln Trp Leu Asp Lys Val Leu Thr Gln Met Gly Ser
                405                 410                 415
Pro Ser Ile Arg Cys Ser Ser Val Ser
            420                 425

<210> SEQ ID NO 9
<211> LENGTH: 552
```

```
<212> TYPE: PRT
<213> ORGANISM: Homo sapiens

<400> SEQUENCE: 9

Met Asp Asn Met Ser Ile Thr Asn Thr Pro Thr Ser Asn Asp Ala Cys
1               5                   10                  15

Leu Ser Ile Val His Ser Leu Met Cys His Arg Gln Gly Gly Glu Ser
            20                  25                  30

Glu Thr Phe Ala Lys Arg Ala Ile Glu Ser Leu Val Lys Lys Leu Lys
        35                  40                  45

Glu Lys Lys Asp Glu Leu Asp Ser Leu Ile Thr Ala Ile Thr Thr Asn
    50                  55                  60

Gly Ala His Pro Ser Lys Cys Val Thr Ile Gln Arg Thr Leu Asp Gly
65                  70                  75                  80

Arg Leu Gln Val Ala Gly Arg Lys Gly Phe Pro His Val Ile Tyr Ala
                85                  90                  95

Arg Leu Trp Arg Trp Pro Asp Leu His Lys Asn Glu Leu Lys His Val
            100                 105                 110

Lys Tyr Cys Gln Tyr Ala Phe Asp Leu Lys Cys Asp Ser Val Cys Val
        115                 120                 125

Asn Pro Tyr His Tyr Glu Arg Val Val Ser Pro Gly Ile Asp Leu Ser
130                 135                 140

Gly Leu Thr Leu Gln Ser Asn Ala Pro Ser Ser Met Met Val Lys Asp
145                 150                 155                 160

Glu Tyr Val His Asp Phe Glu Gly Gln Pro Ser Leu Ser Thr Glu Gly
                165                 170                 175

His Ser Ile Gln Thr Ile Gln His Pro Pro Ser Asn Arg Ala Ser Thr
            180                 185                 190

Glu Thr Tyr Ser Thr Pro Ala Leu Leu Ala Pro Ser Glu Ser Asn Ala
        195                 200                 205

Thr Ser Thr Ala Asn Phe Pro Asn Ile Pro Val Ala Ser Thr Ser Gln
210                 215                 220

Pro Ala Ser Ile Leu Gly Gly Ser His Ser Glu Gly Leu Leu Gln Ile
225                 230                 235                 240

Ala Ser Gly Pro Gln Pro Gly Gln Gln Asn Gly Phe Thr Gly Gln
                245                 250                 255

Pro Ala Thr Tyr His His Asn Ser Thr Thr Thr Trp Thr Gly Ser Arg
            260                 265                 270

Thr Ala Pro Tyr Thr Pro Asn Leu Pro His His Gln Asn Gly His Leu
        275                 280                 285

Gln His His Pro Pro Met Pro Pro His Pro Gly His Tyr Trp Pro Val
    290                 295                 300

His Asn Glu Leu Ala Phe Gln Pro Pro Ile Ser Asn His Pro Ala Pro
305                 310                 315                 320

Glu Tyr Trp Cys Ser Ile Ala Tyr Phe Glu Met Asp Val Gln Val Gly
                325                 330                 335

Glu Thr Phe Lys Val Pro Ser Ser Cys Pro Ile Val Thr Val Asp Gly
            340                 345                 350

Tyr Val Asp Pro Ser Gly Gly Asp Arg Phe Cys Leu Gly Gln Leu Ser
        355                 360                 365

Asn Val His Arg Thr Glu Ala Ile Glu Arg Ala Arg Leu His Ile Gly
    370                 375                 380

Lys Gly Val Gln Leu Glu Cys Lys Gly Glu Gly Asp Val Trp Val Arg
385                 390                 395                 400
```

```
Cys Leu Ser Asp His Ala Val Phe Val Gln Ser Tyr Tyr Leu Asp Arg
                405                 410                 415

Glu Ala Gly Arg Ala Pro Gly Asp Ala Val His Lys Ile Tyr Pro Ser
            420                 425                 430

Ala Tyr Ile Lys Val Phe Asp Leu Arg Gln Cys His Arg Gln Met Gln
            435                 440                 445

Gln Gln Ala Ala Thr Ala Gln Ala Ala Ala Ala Gln Ala Ala Ala
450                 455                 460

Val Ala Gly Asn Ile Pro Gly Pro Gly Ser Val Gly Gly Ile Ala Pro
465                 470                 475                 480

Ala Ile Ser Leu Ser Ala Ala Gly Ile Gly Val Asp Asp Leu Arg
                485                 490                 495

Arg Leu Cys Ile Leu Arg Met Ser Phe Val Lys Gly Trp Gly Pro Asp
                500                 505                 510

Tyr Pro Arg Gln Ser Ile Lys Glu Thr Pro Cys Trp Ile Glu Ile His
            515                 520                 525

Leu His Arg Ala Leu Gln Leu Leu Asp Glu Val Leu His Thr Met Pro
            530                 535                 540

Ile Ala Asp Pro Gln Pro Leu Asp
545                 550

<210> SEQ ID NO 10
<211> LENGTH: 465
<212> TYPE: PRT
<213> ORGANISM: Homo sapiens

<400> SEQUENCE: 10

Met Thr Ser Met Ala Ser Leu Phe Ser Phe Thr Ser Pro Ala Val Lys
1               5                   10                  15

Arg Leu Leu Gly Trp Lys Gln Gly Asp Glu Glu Glu Lys Trp Ala Glu
            20                  25                  30

Lys Ala Val Asp Ala Leu Val Lys Lys Leu Lys Lys Lys Lys Gly Ala
            35                  40                  45

Met Glu Glu Leu Glu Lys Ala Leu Ser Ser Pro Gly Gln Pro Ser Lys
        50                  55                  60

Cys Val Thr Ile Pro Arg Ser Leu Asp Gly Arg Leu Gln Val Ser His
65                  70                  75                  80

Arg Lys Gly Leu Pro His Val Ile Tyr Cys Arg Val Trp Arg Trp Pro
                85                  90                  95

Asp Leu Gln Ser His His Glu Leu Lys Pro Leu Asp Ile Cys Glu Phe
            100                 105                 110

Pro Phe Gly Ser Lys Gln Lys Glu Val Cys Ile Asn Pro Tyr His Tyr
        115                 120                 125

Lys Arg Val Glu Ser Pro Val Leu Pro Pro Val Leu Val Pro Arg His
130                 135                 140

Asn Glu Phe Asn Pro Gln His Ser Leu Leu Val Gln Phe Arg Asn Leu
145                 150                 155                 160

Ser His Asn Glu Pro His Met Pro Gln Asn Ala Thr Phe Pro Asp Ser
                165                 170                 175

Phe His Gln Pro Asn Asn Ala Pro Phe Pro Leu Ser Pro Asn Ser Pro
            180                 185                 190

Tyr Pro Pro Pro Pro Ala Ser Ser Thr Tyr Pro Asn Ser Pro Ala Ser
        195                 200                 205

Ser Gly Pro Gly Ser Pro Phe Gln Leu Pro Ala Asp Thr Pro Pro Pro
```

```
                    210                 215                 220
Ala Tyr Met Pro Pro Asp Asp Gln Met Ala Pro Asp Asn Ser Gln Pro
225                 230                 235                 240
Met Asp Thr Ser Ser Asn Met Ile Pro Gln Thr Met Pro Ser Ile Ser
                245                 250                 255

Ser Arg Asp Val Gln Pro Val Ala Tyr Glu Glu Pro Lys His Trp Cys
                260                 265                 270

Ser Ile Val Tyr Tyr Glu Leu Asn Asn Arg Val Gly Glu Ala Phe His
            275                 280                 285

Ala Ser Ser Thr Ser Val Leu Val Asp Gly Phe Thr Asp Pro Ser Asn
        290                 295                 300

Asn Lys Ser Arg Phe Cys Leu Gly Leu Leu Ser Asn Val Asn Arg Asn
305                 310                 315                 320

Ser Thr Ile Glu Asn Thr Arg Arg His Ile Gly Lys Gly Val His Leu
                325                 330                 335

Tyr Tyr Val Gly Gly Glu Val Tyr Ala Glu Cys Leu Ser Asp Ser Ser
            340                 345                 350

Ile Phe Val Gln Ser Arg Asn Cys Asn Phe His His Gly Phe His Pro
            355                 360                 365

Thr Thr Val Cys Lys Ile Pro Ser Ser Cys Ser Leu Lys Ile Phe Asn
        370                 375                 380

Asn Gln Glu Phe Ala Gln Leu Leu Ala Gln Ser Val Asn His Gly Phe
385                 390                 395                 400

Glu Ala Val Tyr Glu Leu Thr Lys Met Cys Thr Ile Arg Met Ser Phe
                405                 410                 415

Val Lys Gly Trp Gly Ala Glu Tyr His Arg Gln Asp Val Thr Ser Thr
            420                 425                 430

Pro Cys Trp Ile Glu Ile His Leu His Gly Pro Leu Gln Trp Leu Asp
            435                 440                 445

Lys Val Leu Thr Gln Met Gly Ser Pro Leu Asn Pro Ile Ser Ser Val
        450                 455                 460

Ser
465
```